(12) United States Patent
Martin et al.

(10) Patent No.: US 7,595,057 B2
(45) Date of Patent: Sep. 29, 2009

(54) STREPTOCOCCUS PYOGENES ANTIGENS AND CORRESPONDING DNA FRAGMENTS

(75) Inventors: Denis Martin, St Augustin-de Desmaures (CA); Bernard Brodeur, Sillery (CA); Josee Hamel, Sillery (CA); Stephane Rioux, Beauport (CA); Patrick Rheault, St-Etienne-de-Lauzon (CA)

(73) Assignee: ID Biomedical Corporation, Laval (CA)

( * ) Notice: Subject to any disclaimer, the term of this patent is extended or adjusted under 35 U.S.C. 154(b) by 832 days.

(21) Appl. No.: 10/451,337

(22) PCT Filed: Dec. 21, 2001

(86) PCT No.: PCT/CA01/01853

§ 371 (c)(1),
(2), (4) Date: Nov. 18, 2003

(87) PCT Pub. No.: WO02/50107

PCT Pub. Date: Jun. 27, 2002

(65) Prior Publication Data

US 2004/0097706 A1    May 20, 2004

Related U.S. Application Data

(60) Provisional application No. 60/256,940, filed on Dec. 21, 2000.

(51) Int. Cl.
| | |
|---|---|
| A61K 39/09 | (2006.01) |
| A61K 39/38 | (2006.01) |
| A61K 39/00 | (2006.01) |
| C12P 1/00 | (2006.01) |
| A61K 38/00 | (2006.01) |

(52) U.S. Cl. .............. 424/244.1; 424/184.1; 424/185.1; 435/41; 530/300; 530/324

(58) Field of Classification Search .............. 424/184.1, 424/244.1, 93.44; 530/300, 324
See application file for complete search history.

(56) References Cited

U.S. PATENT DOCUMENTS 5,854,416 A * 12/1998 Sampson et al. ........... 536/23.7

FOREIGN PATENT DOCUMENTS

| WO | WO 9952939 | 10/1999 |
|---|---|---|
| WO | WO 0040729 | 7/2000 |
| WO | 02/34771 A2 | 5/2002 |
| WO | 03/051914 A2 | 6/2003 |

OTHER PUBLICATIONS

Bowie et al (Science, 1990, 247:1306-1310).*
Greenspan et al. (Nature Biotechnology 7: 936-937, 1999).*
Lei et al (Infection and Immunity, Dec. 200, p. 6807-6818).*
Ed Harlow et al (Antibodies, A Laboratory Manual, Cold Spring Harbor Laboratory, 1988).*
James C. Smoot et al., "Genome sequence and comparative micoarray analysis of serotype M18 group A *Streptococcus* strains associated with acute rheumatic fever outbreaks," PNAS, Apr. 2, 2002, pp. 4668-4673, vol. 99, No. 7.
Robert Janulczyk et al., "Identification and characterization of a *Streptococcus pyogenes* ABC transporter with multiple specificity for metal cations," Molecular Microbiology, 1999, pp. 596-606, vol. 34, No. 3.
Joseph J. Ferretti et al., "Complete genome sequence of an M1 strain of *Streptococcus pyogenes*," Proc. Natl. Aca. Sci. USA, 2001, pp. 4658-4663, vol. 98.
Database SWALL (Online) EBI, "Hypothetical protein Spy0433 of *S. pyogenes*," Jun. 1, 2001, XP002210908.
Database EMBL (Online), Tamura Y. et al., "*Steptococcus pyogenes* sib38 gene, complete cds," Jan. 12, 2001, XP002219422 & Shigetada Kawabata et al., "A novel anchorless streptococcal surface protein that binds to human immunoglobulins," Biochemical and Biophysical Research Communications, 2002, pp. 1329-1333, vol. 296.

(Continued)

*Primary Examiner*—Robert Mondesi
*Assistant Examiner*—Vanessa L. Ford
(74) *Attorney, Agent, or Firm*—Seed IP Law Group PLLC

(57) ABSTRACT

The present invention relates to antigens, more particularly antigens of *Streptococcus pyogenes* (also called group A *Streptococcus* (GAS)) bacterial pathogen which are useful as vaccine component for therapy and/or prophylaxis.

```
  1 ATGAAAAAGA CATTAACTTT GCTACTGGCA CTCTTTGCCA
    TCGGGGTAAC TAGTAGCGTC

61 AGAGCGGAGG ATGAACAAAG TAGTACACAA AAGCCAGTAA
    AATTTGATTT GGATGGACCT

121 CAACAAAAAA TTAAAGATTA TAGTGGCAAC ACAATCACTC
    TAGAAGACTT ATATGTTGGT

181 AGTAAAGTAG TAAAAATATA TATCCCTCAA GGATGGTGGG
    TATATCTTTA CAGACAATGT

241 GATCATAACA GTAAAGAACG AGGAATTTTA GCTAGTCCTA
    TTCTCGAAAA AAATATAACA

301 AAAACAGATC CTTATCGTCA ATATTATACA GGAGTACCTT
    ATATTCTTAA CTTAGGAGAA

361 GATCCTTTGA AGAAAGGAGA AAAATTAACT TTCTCATTTA
    AAGGAGAAGA CGGATTTTAT

421 GTCGGTAGCT ATATCTATAG AGACTCTGAT ACTATAAAAA
    AAGAAAAAGA AGCTGAAGAA

481 GCACTTCAAA AAAAGGAAGA GGAAAAGCAA CAAAACAGC
    TAGAAGAAAG CATGCTAAAG

541 CAGATAAGAG AAGAAGACCA TAAACCTTGG CATCAGCGGT
    TAAGTGAGAG CATCCAAGAT

601 CAGTGGTGGA ACTTTAAGGG AQTGTTTCAG TGA
```

12 Claims, 7 Drawing Sheets

OTHER PUBLICATIONS

Database EMBL (Online), Ferretti J. J. et al., "*Streptococcus pyogenes* M1 GAS strain SF370. section 65 of 167 of the complete genome," Apr. 16, 2001, XP002219423; Joseph J. Ferreti et al., "Complete genome sequence of an M1 strain of *Streptococcus pyogenes*," Proc. Natl. Aca. Sci. USA, Apr. 10, 2001, pp. 4658-4663, vol. 98, No. 8, XP002168716.

Kil, K. S. et al., "Cloning and sequence analysis of a gene encoding a 67-kilodalton myosin-cross-reactive antigen of *Streptococcus pyogenes* reveals its similartiy with class II major histocompatibility antigens," Infection and Immunity, Jun. 1994, pp. 2440-2449, vol. 62, No. 6.

Geneseq Database (STN online), Accession No. AAO30967, Jun. 26, 2003.

Geneseq Database (STN online), Accession No. ABP29294, May 2, 2002.

Cunningham, "Pathogenesis of Group A Streptococcal Infections", Clinical Microbiology Reviews, 13(3):470-511, Jul. 2000.

Jameson and Wolf, "The antigenic index: a novel algorithm for predicting antigenic determinants," Computer Application Bioscience, 4(1):181-186, 1988.

Roitt et al., Immunology, 4th edition, 1998, p. 7.7-7.8, Mosby, London.

Wan et al., "Epitope Map for a Growth Hormone Receptor Agonist Monoclonal Antibody, MAb 263," Molecular Endocrinology, 17(11):2240-2250, 2003.

* cited by examiner

Figure 1; SEQ ID NO: 1.

```
  1 ATGAAAAAGA CATTAACTTT GCTACTGGCA CTCTTTGCCA TCGGGGTAAC TAGTAGCGTC
 61 AGAGCGGAGG ATGAACAAAG TAGTACACAA AAGCCAGTAA AATTTGATTT GGATGGACCT
121 CAACAAAAAA TTAAAGATTA TAGTGGCAAC ACAATCACTC TAGAAGACTT ATATGTTGGT
181 AGTAAAGTAG TAAAAATATA TATCCCTCAA GGATGGTGGG TATATCTTTA CAGACAATGT
241 GATCATAACA GTAAAGAACG AGGAATTTTA GCTAGTCCTA TTCTCGAAAA AAATATAACA
301 AAAACAGATC CTTATCGTCA ATATTATACA GGAGTACCTT ATATTCTTAA CTTAGGAGAA
361 GATCCTTTGA AGAAGGAGA AAAATTAACT TTCTCATTTA AGGAGAAGA CGGATTTTAT
421 GTCGGTAGCT ATATCTATAG AGACTCTGAT ACTATAAAAA AAGAAAAAGA AGCTGAAGAA
481 GCACTTCAAA AAAAGGAAGA GGAAAAGCAA CAAAAACAGC TAGAAGAAAG CATGCTAAAG
541 CAGATAAGAC AAGAAGACCA TAAACCTTGG CATCAGCGGT TAAGTGAGAG CATCCAAGAT
601 CAGTGGTGGA ACTTTAAGGG ACTGTTTCAG TGA
```

Figure 2; SEQ ID NO: 2

```
  1 MKKTLTLLLA LFAIGVTSSV RAEDEQSSTQ KPVKFDLDGP QQKIKDYSGN TITLEDLYVG
 61 SKVVKIYIPQ GWWVYLYRQC DHNSKERGIL ASPILEKNIT KTDPYRQYYT GVPYILNLGE
121 DPLKKGEKLT FSFKGEDGFY VGSYIYRDSD TIKKEKEAEE ALQKKEEEKQ QKQLEESMLK
181 QIREEDHKPW HQRLSESIQD QWWNFKGLFQ
```

Figure 3; SEQ ID NO: 3.

```
  1 ATGAGCCTCA TTTTGGGTGC TTTTTTATCT GTTTTTCTTT TAGTAGCTTG TTCGTCAACT
 61 GGCACTAAAA CTGCTAAGAG TGATAAATTA AAAGTCGTGG CAACCAATTC AATTATTGCC
121 GACATGACAA AAGCTATTGC TGGTGATAAA ATCGATCTGC ACAGCATTGT GCCAATCGGT
181 CAAGACCCTC ATGAGTACGA ACCATTACCA GAAGATGTTG AAAAAACAAG TAATGCTGAT
241 GTGATTTTCT ATAATGGTAT CAATCTAGAA GATGGCGGGC AAGCTTGGTT CACCAAACTA
301 GTGAAAAATG CTCAAAAAAC GAAAAACAAA GATTACTTTG CCGTGTCTGA TGGCATTGAT
361 GTGATTTACT TGGAAGGTGC AAGCGAAAAA GGAAAAGAAG ATCCACATGC TTGGTTAAAT
421 CTCGAAAACG GAATCATTTA TTCAAAAAAC ATTGCCAAAC AATTGATTGC AAAGGATCCT
481 AAAAACAAAG AAACTTATGA AAAGAACCTA AAGCTTATG TGGCTAAATT GGAAAAACTA
541 GACAAAGAAG CCAAATCAAA ATTTGATGCT ATTGCAGAAA ATAAAAAATT GATTGTGACT
601 AGTGAAGGCT GCTTCAAGTA CTTTTCAAAA GCTTACGGTG TCCCATCTGC TTATATCTGG
661 GAAATTAACA CCGAAGAAGA AGGAACACCA GATCAAATTT CATCATTGAT TGAAAAACTA
721 AAAGTCATCA AGCCATCTGC GCTTTTTGTA GAGTCAAGTG TCGATAGACG CCCTATGGAA
781 ACTGTTTCTA AAGATAGTGG TATTCCTATT TATTCTGAGA TCTTTACAGA TTCAATTGCT
841 AAAAAAGGTA AACCTGGCGA TAGTTATTAT GCTATGATGA AATGGAACCT TGACAAAATT
901 TCTGAAGGTC TAGCAAAATA A
```

Figure 4; SEQ ID NO: 4

```
  1 MSLILGAFLS VFLLVACSST GTKTAKSDKL KVVATNSIIA DMTKAIAGDK IDLHSIVPIG
 61 QDPHEYEPLP EDVEKTSNAD VIFYNGINLE DGGQAWFTKL VKNAQKTKNK DYFAVSDGID
121 VIYLEGASEK GKEDPHAWLN LENGIIYSKN IAKQLIAKDP KNKETYEKNL KAYVAKLEKL
181 DKEAKSKFDA IAENKKLIVT SEGCFKYFSK AYGVPSAYIW EINTEEEGTP DQISSLIEKL
241 KVIKPSALFV ESSVDRRPME TVSKDSGIPI YSEIFTDSIA KKGKPGDSYY AMMKWNLDKI
301 SEGLAK
```

Figure 5; SEQ ID NO: 5.

```
  1 ATGAACAAGA AATTTATTGG TCTTGGTTTA GCGTCAGTGG CTGTGCTGAG TTTAGCTGCT
 61 TGTGGTAATC GTGGTGCTTC TAAAGGTGGG GCATCAGGAA AAACTGATTT AAAAGTTGCA
121 ATGGTTACCG ATACTGGTGG TGTAGATGAC AAATCATTCA ACCAATCAGC ATGGGAAGGC
```

```
181  CTGCAATCTT GGGGTAAAGA AATGGGCCTT CAAAAAGGAA CAGGTTTCGA TTATTTTCAA
241  TCTACAAGTG AATCTGAGTA TGCAACTAAT CTCGATACAG CAGTTTCAGG AGGGTATCAA
301  CTGATTTATG GTATCGGCTT TGCATTGAAA GATGCTATTG CTAAAGCAGC TGGAGATAAT
361  GAAGGAGTTA AGTTTGTTAT TATCGATGAT ATTATCGAAG GAAAAGATAA TGTAGCCAGT
421  GTTACCTTTG CCGACCATGA AGCTGCTTAT CTTGCAGGAA TTGCAGCTGC AAAAACAACA
481  AAAACAAAAA CAGTTGGTTT CGTGGGCGGT ATGGAAGGAA CTGTCATAAC TCGATTTGAA
541  AAAGGTTTTG AAGCAGGAGT TAAGTCTGTT GACGATACAA TCCAAGTTAA AGTTGATTAT
601  GCTGGATCAT TTGGTGACGC TGCAAAAGGA AAAACAATCG CAGCAGCTCA GTATGCAGCA
661  GGTGCTGATG TTATTTACCA GGCAGCAGGA GGCACTGGAG CAGGTGTATT TAATGAAGCA
721  AAAGCTATTA ATGAAAAACG TAGTGAAGCT GATAAAGTTT GGGTTATTGG TGTTGACCGT
781  GATCAAAAAG ACGAAGGAAA ATACACTTCT AAAGATGGCA AAGAAGCAAA CTTTGTACTT
841  GCATCATCAA TCAAAGAAGT CGGTAAAGCT GTTCAGTTAA TCAACAAGCA AGTAGCAGAT
901  AAAAAATTCC CTGGAGGAAA AACAACTGTC TATGGTCTAA AGATGGCGG TGTTGAAATC
961  GCAACTACAA ATGTTTCAAA AGAAGCTGTT AAAGCTATTA AGAAGCGAA AGCAAAAATT
1021 AAATCTGGTG ACATTAAAGT TCCTGAAAAA TAG
```

Figure 6; SEQ ID NO: 6

```
  1 MNKKFIGLGL ASVAVLSLAA CGNRGASKGG ASGKTDLKVA MVTDTGGVDD KSFNQSAWEG
 61 LQSWGKEMGL QKGTGFDYFQ STSESEYATN LDTAVSGGYQ LIYGIGFALK DAIAKAAGDN
121 EGVKFVIIDD IIEGKDNVAS VTFADHEAAY LAGIAAAKTT KTKTVGFVGG MEGTVITRFE
181 KGFEAGVKSV DDTIQVKVDY AGSFGDAAKG KTIAAAQYAA GADVIYQAAG GTGAGVFNEA
241 KAINEKRSEA DKVWVIGVDR DQKDEGKYTS KDGKEANFVL ASSIKEVGKA VQLINKQVAD
301 KKFPGGKTTV YGLKDGGVEI ATTNVSKEAV KAIKEAKAKI KSGDIKVPEK
```

Figure 7; SEQ ID NO: 7.

```
  1 ATGAACAAAA AAGTAATGTC ACTTGGTCTT GTTTCGACTG CCCTATTCAC ATTAGGAGGC
 61 TGTACCAATA ACTCCGCTAA ACAAACAACT GACAATTCAT TAAAAATCGC TATGATTACT
121 AATCAGACGG GTATTGATGA CAAGTCATTT AACCAGTCAG CCTGGGAAGG CTTACAAGCT
181 TGGGGAAAAG AAAATAAACT TGAAAAGGA AAAGGCTATG ATTATTTCCA ATCAGCCAAT
241 GAATCAGAGT TTACCACAAA CCTTGAGTCA GCAGTAACCA ATGGTTATAA TCTTGTTTTT
301 GGGATTGGAT TTCCATTACA TGACGCTGTA GAAAAAGTAG CCGCAAACAA TCCTGACAAC
361 CATTTTGCAA TTGTGGATGA TGTGATTAAA GGTCAAAAAA ATGTTGCAAG TATCACCTTT
421 TCAGACCATG AAGCGGCATA CCTAGCCGGT GTTGCAGCAG CTAAAACGAC AAAAACCAAG
481 CAAGTTGGTT TTGTAGGTGG TATGGAAGGA GATGTTGTCA AGCGCTTTGA AAAAGGTTTT
541 GAAGCTGGTG TGAAATCAGT AGATGATACC ATCAAAGTAA GAGTTGCTTA TGCAGGCTCT
601 TTTGCAGATG CTGCCAAAGG CAAGACGATT GCAGCTGCTC AATACGCTGA AGGCGCAGAT
661 GTTATTTATC ATGCAGCAGG AGGCACAGGG GCGGGTGTCT TTAGCGAAGC TAAGTCTATC
721 AACGAAAAAC GTAAAGAAGA AGATAAGGTT TGGGTTATTG GTGTTGACCG TGACCAAAGT
781 GAAGATGGAA AATACACTAC AAAAGATGGC AAGTCAGCTA ATTTTGTTTT GACCTCAAGT
841 ATCAAGGAAG TCGGAAAAGC TTTAGTAAAA GTAGCCGTAA AAACCTCAGA AGACCAATTC
901 CCAGGTGGTC AAATAACCAC TTTTGGTTTA AAAGAAGGTG GTGTTAGCCT TACAACGGAT
961 GCTCTGACAC AAGACACTAA AAAAGCTATT GAGGCTGCTA AAAAAGCGAT TATCGAAGGA
1021 ACCATCACAG TTCCTGAAAA CTAA
```

Figure 8; SEQ ID NO: 8

```
  1 MNKKVMSLGL VSTALFTLGG CTNNSAKQTT DNSLKIAMIT NQTGIDDKSF NQSAWEGLQA
 61 WGKENKLEKG KGYDYFQSAN ESEFTTNLES AVTNGYNLVF GIGFPLHDAV EKVAANNPDN
121 HFAIVDDVIK GQKNVASITF SDHEAAYLAG VAAAKTTKTK QVGFVGGMEG DVVKRFEKGF
181 EAGVKSVDDT IKVRVAYAGS FADAAKGKTI AAAQYAEGAD VIYHAAGGTG AGVFSEAKSI
241 NEKRKEEDKV WVIGVDRDQS EDGKYTTKDG KSANFVLTSS IKEVGKALVK VAVKTSEDQF
301 PGGQITTFGL KEGGVSLTTD ALTQDTKKAI EAAKKAIIEG TITVPEN
```

Figure 9; SEQ ID NO: 9.

```
  1 ATGAGAAAAA GATGCTATTC AACTTCAGCT GCAGTATTGG CAGCAGTGAC TTTATTTGTT
 61 CTATCGGTAG ATCGTGGTGT TATAGCAGAT AGTTTTTCTG CTAATCAAGA GATTAGATAT
121 TCGGAAGTAA CACCTTATCA CGTTACTTCC GTTTGGACCA AAGGAGTTAC TCCTCCAGCA
181 AACTTCACTC AAGGTGAAGA TGTTTTTCAC GCTCCTTATG TTGCTAACCA AGGATGGTAT
241 GATATTACCA AAACATTCAA TGGAAAAGAC GATCTTCTTT GCGGGGCTGC CACAGCAGGG
301 AATATGCTTC ACTGGTGGTT CGATCAAAAC AAAGACCAAA TTAAACGTTA TTTGGAAGAG
361 CATCCAGAAA AGCAAAAAAT AAACTTCAAT GGCGAACAGA TGTTTGACGT AAAAGAAGCT
421 ATCGACACTA AAACCACCA GCTAGATAGT AAATTATTTG AATATTTTAA AGAAAAAGCT
481 TTCCCTTATC TATCTACTAA ACACCTAGGA GTTTTCCCTG ATCATGTAAT TGATATGTTC
541 ATTAACGGCT ACCGCCTTAG TCTAACTAAC CACGGTCCAA CGCCAGTAAA AGAAGGTAGT
601 AAAGATCCCC GAGGTGGTAT TTTTGACGCC GTATTTACAA GAGGTGATCA AAGTAAGCTA
661 TTGACAAGTC GTCATGATTT TAAAGAAAAA AATCTCAAAG AAATCAGTGA TCTCATTAAG
721 AAAGAGTTAA CCGAAGGCAA GGCTCTAGGC CTATCACACA CCTACGCTAA CGTACGCATC
781 AACCATGTTA TAAACCTGTG GGGAGCTGAC TTTGATTCTA ACGGGAACCT TAAAGCTATT
841 TATGTAACAG ACTCTGATAG TAATGCATCT ATTGGTATGA AGAAATACTT TGTTGGTGTT
901 AATTCCGCTG GAAAAGTAGC TATTTCTGCT AAAGAAATAA AAGAAGATAA TATTGGTGCT
961 CAAGTACTAG GGTTATTTAC ACTTTCAACA GGGCAAGATA GTTGGAATCA GACCAATTAA
```

Figure 10; SEQ ID NO: 10

```
  1 MRKRCYSTSA AVLAAVTLFV LSVDRGVIAD SFSANQEIRY SEVTPYHVTS VWTKGVTPPA
 61 NFTQGEDVFH APYVANQGWY DITKTFNGKD DLLCGAATAG NMLHWWFDQN KDQIKRYLEE
121 HPEKQKINFN GEQMFDVKEA IDTKNHQLDS KLFEYFKEKA FPYLSTKHLG VFPDHVIDMF
181 INGYRLSLTN HGPTPVKEGS KDPRGGIFDA VFTRGDQSKL LTSRHDPKEK NLKEISDLIK
241 KELTEGKALG LSHTYANVRI NHVINLWGAD FDSNGNLKAI YVTDSDSNAS IGMKKYFVGV
301 NSAGKVAISA KEIKEDNIGA QVLGLFTLST GQDSWNQTN
```

Figure 11; SEQ ID NO: 11.

```
  1 TCTTGGTTTA GCGTCAGTGG CTGTGCTGAG TTTAGCTGCT TGTGGTAATC GTGGTGCTTC
 61 TAAAGGTGGG GCATCAGGAA AAACTGATTT AAAAGTTGCA ATGGTTACCG ATACTGGTGG
121 TGTAGATGAC AAATCATTCA ACCAATCAGC ATGGGAAGGC CTGCAATCTT GGGGTAAAGA
181 AATGGGCCTT CAAAAAGGAA CAGGTTTCGA TTATTTTCAA TCTACAAGTG AATCTGAGTA
241 TGCAACTAAT CTTGATACAG CAGTTTCAGG AGGGTATCAA CTGATTTATG GTATCGGCTT
301 TGCATTGAAA GATGCTATTG CTAAAGCAGC TGGAGATAAT GAAGGAGTTA AGTTTGTTAT
361 TATCGATGAT ATTATCGAAG GAAAAGATAA TGTAGCCAGT GTTACCTTTG CTGACCATGA
421 AGCTGCTTAT CTTGCAGGAA TTGCAGCTGC AAAAACAACA AAAACAAAAA CAGTTGGTTT
481 CGTGGGCGGT ATGGAAGGAA CTGTCATAAC TCGATTTGAA AAAGGTTTTG AAGCAGGAGT
541 TAAGTCTGTT GACGATACAA TCCAAGTTAA AGTTGATTAT GCTGGATCAT TTGGTGACGC
601 TGCAAAAGGA AAAACAATCG CAGCAGCTCA GTATGCAGCA GGTGCTGATG TTATTTACCA
661 GGCAGCAGGA GGCACTGGAG CAGGTGTATT TAATGAAGCA AAAGCTATTA ATGAAAAACG
721 TAGTGAAGCT GATAAAGTTT GGGTTATTGG TGTTGACCGT GATCAAAAAG ACGAAGGAAA
781 ATACACTTCT AAAGATGGCA AAGAAGCAAA CTTTGTACTT GCATCATCAA TCAAAGAAGT
841 TGGTAAAGCT GTTCAGTTAA TCAACAAACA AGTAGCAGAT AAAAAATTCC CTGGAGGAAA
901 AACAACTGTC TATGGTCTAA AGATGGCGG TGTTGAAATC GCAACTACAA ATGTTTCAAA
961 AGAAGCTGTT AAAGCTATTA AGAAGCGAA AGC
```

Figure 12; SEQ ID NO: 12.

```
  1 LGLASVAVLS LAACGNRGAS KGGASGKTDL KVAMVTDTGG VDDKSFNQSA WEGLQSWGKE
 61 MGLQKGTGFD YFQSTSESEY ATNLDTAVSG GYQLIYGIGF ALKDAIAKAA GDNEGVKFVI
121 IDDIIEGKDN VASVTFADHE AAYLAGIAAA KTTKTKTVGF VGGMEGTVIT RFEKGFEAGV
181 KSVDDTIQVK VDYAGSFGDA AKGKTIAAAQ YAAGADVIYQ AAGGTGAGVP NEAKAINEKR
241 SEADKVWVIG VDRDQKDEGK YTSKDGKEAN FVLASSIKEV GKAVQLINKQ VADKKFPGGK
```

Figure 13; SEQ ID NO: 13.

```
  1 TCTTGGTTTA GCGTCAGTGG CTGTGCTGAG TTTAGCTGCT TGTGGTAATC GTGGTGCTTC
 61 TAAAGGTGGG GCATCAGGAA AAACTGATTT AAAAGTTGCA ATGGTTACCG ATACTGGTGG
121 TGTAGATGAC AAATCATTCA ACCAATCAGC ATGGGAAGGC CTGCAATCTT GGGGTAAAGA
181 AATGGGCCTT CAAAAAGGAA CAGGTTTCGA TTATTTTCAA TCTACAAGTG AATCTGAGTA
241 TGCAACTAAT CTCGATACAG CAGTTTCAGG AGGATATCAA CTGATTTATG GTATCGGCTT
301 TGCATTGAAA GATGCTATTG CTAAAGCAGC TGGAGATAAT GAAGGAGTTA AGTTTGTTAT
361 TATCGATGAT ATTATCGAAG GAAAAGATAA TGTAGCCAGT GTTACCTTTG CCGACCATGA
421 AGCTGCTTAT CTTGCAGGAA TTGCGGCTGC AAAAACAACA AAAACAAAAA CAGTTGGTTT
481 CGTGGGCGGT ATGGAAGGAA CTGTCATAAC TCGATTTGAA AAAGGTTTTG AAGCAGGAGT
541 TAAGTCTGTT GACGATACAA TCCAAGTTAA AGTTGATTAT GCTGGATCAT TTGGTGACGC
601 TGCAAAAGGA AAAACAATCG CAGCAGCTCA GTATGCAGCA GGTGCTGATG TTATTTACCA
661 GGCAGCAGGA GGCACTGGAG CAGGTGTATT TAATGAAGCA AAAGCTATTA ATGAAAAACG
721 TAGTGAAGCT GATAAAGTTT GGGTTATTGG TGTTGACCGT GATCAAAAAG ACGAAGGAAA
781 ATACACTTCT AAAGATGGCA AAGAAGCAAA CTTTGTACTT GCATCATCAA TCAAAGAAGT
841 TGGTAAAGCT GTTCAGTTAA TCAACAAACA AGTAGCAGAT AAAAAATTCC CTGGAGGAAA
901 AACAACTGTC TATGGTTTAA AGATGGCGG TGTTGAAATC GCAACTACAA ATGTTTCAAA
961 AGAAGCTGTT AAAGCTATTA AGAAGCGAA AGC
```

Figure 14; SEQ ID NO: 14.

```
  1 LGLASVAVLS LAACGNRGAS KGGASGKTDL KVAMVTDTGG VDDKSFNQSA WEGLQSWGKE
 61 MGLQKGTGFD YFQSTSESEY ATNLDTAVSG GYQLIYGIGF ALKDAIAKAA GDNEGVKFVI
121 IDDIIEGKDN VASVTFADHE AAYLAGIAAA KTTKTKTVGF VGGMEGTVIT RFEKGFEAGV
181 KSVDDTIQVK VDYAGSFGDA AKGKTIAAAQ YAAGADVIYQ AAGGTGAGVF NEAKAINEKR
241 SEADKVWVIG VDRDQKDEGK YTSKDGKEAN FVLASSIKEV GKAVQLINKQ VADKKFPGGK
301 TTVYGLKDGG VEIATTNVSK EAVKAIKEAK
```

Figure 15; SEQ ID NO: 15.

```
  1 TCTTGGTTTA GCGTCAGTGG CTGTGCTGAG TTTAGCTGCT TGTGGTAATC GTGGTGCTTC
 61 TAAAGGTGGG GCAGCAGGAA AAACTGATTT AAAAGTTGCA ATGGTTACCG ATACTGGTGG
121 TGTAGATGAT AAATCATTCA ACCAATCAGC ATGGGAAGGC CTGCAATCTT GGGGTAAAGA
181 AATGGGCCTT CAAAAAGGAA CAGGTTTCGA TTATTTTCAA TCTACAAGTG AATCTGAGTA
241 TGCAACTAAT CTCGATACAG CAGTTTCAGG AGGGTATCAA CTGATTTATG GTATCGGCTT
301 TGCATTGAAA GATGCTATTG CTAAAGCAGC TGGAGATAAT GAAGGAGTTA AGTTTGTTAT
361 TATCGATGAT ATTATCGAAG GAAAAGATAA TGTAGCCAGT GTTACCTTTG CCGACCATGA
421 AGCTGCTTAT CTTGCAGGAA TTGCAGCTGC AAAAACAACA AAAACAAAAA CAGTTGGTTT
481 CGTGGGCGGT ATGGAAGGAA CTGTCATAAC TCGATTTGAA AAAGGTTTTG AAGCAGGAGT
541 TAAGTCTGTT GACGATACAA TCCAAGTTAA AGTTGATTAT GCTGGATCAT TTGGTGACGC
601 TGCAAAAGGA AAAACAATCG CAGCAGCTCA GTATGCAGCA GGTGCTGATG TTATTTACCA
661 GGCAGCAGGA GGCACTGGAG CAGGTGTATT TAATGAAGCA AAAGCTATTA ATGAAAAACG
721 TAGTGAAGCT GATAAAGTTT GGGTTATTGG TGTTGACCGT GATCAAAAAG ACGAAGGAAA
781 ATACACTTCT AAAGATGGCA AAGAAGCAAA CTTTGTACTT GCATCATCAA TCAAAGAAGT
841 TGGTAAAGCT GTTCAGTTAA TCAACAAGCA AGTAGCAGAT AAAAAATTCC CTGGAGGAAA
901 AACAACTGTC TATGGTCTAA AGATGGCGG TGTTGAAATC GCAACTACAA ATGTTTCAAA
961 AGAAGCTGTT AAAGCTATTA AGAAGCGAA AGC
```

Figure 16; SEQ ID NO: 16.

```
  1 LGLASVAVLS LAACGNRGAS KGGAAGKTDL KVAMVTDTGG VDDKSFNQSA WEGLQSWGKE
 61 MGLQKGTGFD YFQSTSESEY ATNLDTAVSG GYQLIYGIGF ALKDAIAKAA GDNEGVKFVI
```

Figure 17

```
700294    1 TCTTGGTTTAGCGTCAGTGGCTGTGCTGAGTTTAGCTGCTTGTGGTAATC   50
12384     1 TCTTGGTTTAGCGTCAGTGGCTGTGCTGAGTTTAGCTGCTTGTGGTAATC   50
SPY67     1 TCTTGGTTTAGCGTCAGTGGCTGTGCTGAGTTTAGCTGCTTGTGGTAATC   50
B514      1 TCTTGGTTTAGCGTCAGTGGCTGTGCTGAGTTTAGCTGCTTGTGGTAATC   50
            **************************************************

700294   51 GTGGTGCTTCTAAAGGTGGGGCATCAGGAAAAACTGATTTAAAAGTTGCA  100
12384    51 GTGGTGCTTCTAAAGGTGGGGCATCAGGAAAAACTGATTTAAAAGTTGCA  100
SPY67    51 GTGGTGCTTCTAAAGGTGGGGCATCAGGAAAAACTGATTTAAAAGTTGCA  100
B514     51 GTGGTGCTTCTAAAGGTGGGGCAGCAGGAAAAACTGATTTAAAAGTTGCA  100
            ***********************  *************************

700294  101 ATGGTTACCGATACTGGTGGTGTAGATGACAAATCATTCAACCAATCAGC  150
12384   101 ATGGTTACCGATACTGGTGGTGTAGATGACAAATCATTCAACCAATCAGC  150
SPY67   101 ATGGTTACCGATACTGGTGGTGTAGATGACAAATCATTCAACCAATCAGC  150
B514    101 ATGGTTACCGATACTGGTGGTGTAGATGATAAATCATTCAACCAATCAGC  150
            ***************************** ********************

700294  151 ATGGGAAGGCCTGCAATCTTGGGGTAAAGAAATGGGCCTTCAAAAAGGAA  200
12384   151 ATGGGAAGGCCTGCAATCTTGGGGTAAAGAAATGGGCCTTCAAAAAGGAA  200
SPY67   151 ATGGGAAGGCCTGCAATCTTGGGGTAAAGAAATGGGCCTTCAAAAAGGAA  200
B514    151 ATGGGAAGGCCTGCAATCTTGGGGTAAAGAAATGGGCCTTCAAAAAGGAA  200
            **************************************************

700294  201 CAGGTTTCGATTATTTTCAATCTACAAGTGAATCTGAGTATGCAACTAAT  250
12384   201 CAGGTTTCGATTATTTTCAATCTACAAGTGAATCTGAGTATGCAACTAAT  250
SPY67   201 CAGGTTTCGATTATTTTCAATCTACAAGTGAATCTGAGTATGCAACTAAT  250
B514    201 CAGGTTTCGATTATTTTCAATCTACAAGTGAATCTGAGTATGCAACTAAT  250
            **************************************************

700294  251 CTCGATACAGCAGTTTCAGGAGGGTATCAACTGATTTATGGTATCGGCTT  300
12384   251 CTTGATACAGCAGTTTCAGGAGGGTATCAACTGATTTATGGTATCGGCTT  300
SPY67   251 CTCGATACAGCAGTTTCAGGAGGATATCAACTGATTTATGGTATCGGCTT  300
B514    251 CTCGATACAGCAGTTTCAGGAGGGTATCAACTGATTTATGGTATCGGCTT  300
            ** ******************** **************************

700294  301 TGCATTGAAAGATGCTATTGCTAAAGCAGCTGGAGATAATGAAGGAGTTA  350
12384   301 TGCATTGAAAGATGCTATTGCTAAAGCAGCTGGAGATAATGAAGGAGTTA  350
SPY67   301 TGCATTGAAAGATGCTATTGCTAAAGCAGCTGGAGATAATGAAGGAGTTA  350
B514    301 TGCATTGAAAGATGCTATTGCTAAAGCAGCTGGAGATAATGAAGGAGTTA  350
            **************************************************

700294  351 AGTTTGTTATTATCGATGATATTATCGAAGGAAAAGATAATGTAGCCAGT  400
12384   351 AGTTTGTTATTATCGATGATATTATCGAAGGAAAAGATAATGTAGCCAGT  400
SPY67   351 AGTTTGTTATTATCGATGATATTATCGAAGGAAAAGATAATGTAGCCAGT  400
B514    351 AGTTTGTTATTATCGATGATATTATCGAAGGAAAAGATAATGTAGCCAGT  400
            **************************************************

700294  401 GTTACCTTTGCCGACCATGAAGCTGCTTATCTTGCAGGAATTGCAGCTGC  450
12384   401 GTTACCTTTGCTGACCATGAAGCTGCTTATCTTGCAGGAATTGCAGCTGC  450
SPY67   401 GTTACCTTTGCCGACCATGAAGCTGCTTATCTTGCAGGAATTGCGGCTGC  450
B514    401 GTTACCTTTGCCGACCATGAAGCTGCTTATCTTGCAGGAATTGCAGCTGC  450
            *********** ******************************* *****

700294  451 AAAAACAACAAAAACAAAAACAGTTGGTTTCGTGGGCGGTATGGAAGGAA  500
12384   451 AAAAACAACAAAAACAAAAACAGTTGGTTTCGTGGGCGGTATGGAAGGAA  500
SPY67   451 AAAAACAACAAAAACAAAAACAGTTGGTTTCGTGGGCGGTATGGAAGGAA  500
B514    451 AAAAACAACAAAAACAAAAACAGTTGGTTTCGTGGGCGGTATGGAAGGAA  500
            **************************************************
```

```
700294  501  CTGTCATAACTCGATTTGAAAAAGGTTTTGAAGCAGGAGTTAAGTCTGTT  550
12384   501  CTGTCATAACTCGATTTGAAAAAGGTTTTGAAGCAGGAGTTAAGTCTGTT  550
SPY67   501  CTGTCATAACTCGATTTGAAAAAGGTTTTGAAGCAGGAGTTAAGTCTGTT  550
B514    501  CTGTCATAACTCGATTTGAAAAAGGTTTTGAAGCAGGAGTTAAGTCTGTT  550
             **************************************************

700294  551  GACGATACAATCCAAGTTAAAGTTGATTATGCTGGATCATTTGGTGACGC  600
12384   551  GACGATACAATCCAAGTTAAAGTTGATTATGCTGGATCATTTGGTGACGC  600
SPY67   551  GACGATACAATCCAAGTTAAAGTTGATTATGCTGGATCATTTGGTGACGC  600
B514    551  GACGATACAATCCAAGTTAAAGTTGATTATGCTGGATCATTTGGTGACGC  600
             **************************************************

700294  601  TGCAAAAGGAAAAACAATCGCAGCAGCTCAGTATGCAGCAGGTGCTGATG  650
12384   601  TGCAAAAGGAAAAACAATCGCAGCAGCTCAGTATGCAGCAGGTGCTGATG  650
SPY67   601  TGCAAAAGGAAAAACAATCGCAGCAGCTCAGTATGCAGCAGGTGCTGATG  650
B514    601  TGCAAAAGGAAAAACAATCGCAGCAGCTCAGTATGCAGCAGGTGCTGATG  650
             **************************************************

700294  651  TTATTTACCAGGCAGCAGGAGGCACTGGAGCAGGTGTATTTAATGAAGCA  700
12384   651  TTATTTACCAGGCAGCAGGAGGCACTGGAGCAGGTGTATTTAATGAAGCA  700
SPY67   651  TTATTTACCAGGCAGCAGGAGGCACTGGAGCAGGTGTATTTAATGAAGCA  700
B514    651  TTATTTACCAGGCAGCAGGAGGCACTGGAGCAGGTGTATTTAATGAAGCA  700
             **************************************************

700294  701  AAAGCTATTAATGAAAAACGTAGTGAAGCTGATAAAGTTTGGGTTATTGG  750
12384   701  AAAGCTATTAATGAAAAACGTAGTGAAGCTGATAAAGTTTGGGTTATTGG  750
SPY67   701  AAAGCTATTAATGAAAAACGTAGTGAAGCTGATAAAGTTTGGGTTATTGG  750
B514    701  AAAGCTATTAATGAAAAACGTAGTGAAGCTGATAAAGTTTGGGTTATTGG  750
             **************************************************

700294  751  TGTTGACCGTGATCAAAAAGACGAAGGAAAATACACTTCTAAAGATGGCA  800
12384   751  TGTTGACCGTGATCAAAAAGACGAAGGAAAATACACTTCTAAAGATGGCA  800
SPY67   751  TGTTGACCGTGATCAAAAAGACGAAGGAAAATACACTTCTAAAGATGGCA  800
B514    751  TGTTGACCGTGATCAAAAAGACGAAGGAAAATACACTTCTAAAGATGGCA  800
             **************************************************

700294  801  AAGAAGCAAACTTTGTACTTGCATCATCAATCAAAGAAGTCGGTAAAGCT  850
12384   801  AAGAAGCAAACTTTGTACTTGCATCATCAATCAAAGAAGTTGGTAAAGCT  850
SPY67   801  AAGAAGCAAACTTTGTACTTGCATCATCAATCAAAGAAGTTGGTAAAGCT  850
B514    801  AAGAAGCAAACTTTGTACTTGCATCATCAATCAAAGAAGTTGGTAAAGCT  850
             ****************************************  ********

700294  851  GTTCAGTTAATCAACAAGCAAGTAGCAGATAAAAAATTCCCTGGAGGAAA  900
12384   851  GTTCAGTTAATCAACAAACAAGTAGCAGATAAAAAATTCCCTGGAGGAAA  900
SPY67   851  GTTCAGTTAATCAACAAACAAGTAGCAGATAAAAAATTCCCTGGAGGAAA  900
B514    851  GTTCAGTTAATCAACAAGCAAGTAGCAGATAAAAAATTCCCTGGAGGAAA  900
             *****************  *******************************

700294  901  AACAACTGTCTATGGTCTAAAAGATGGCGGTGTTGAAATCGCAACTACAA  950
12384   901  AACAACTGTCTATGGTCTAAAAGATGGCGGTGTTGAAATCGCAACTACAA  950
SPY67   901  AACAACTGTCTATGGTTTAAAAGATGGCGGTGTTGAAATCGCAACTACAA  950
B514    901  AACAACTGTCTATGGTCTAAAAGATGGCGGTGTTGAAATCGCAACTACAA  950
             ****************  ********************************

700294  951  ATGTTTCAAAAGAAGCTGTTAAAGCTATTAAAGAAGCGAAAGC  993
12384   951  ATGTTTCAAAAGAAGCTGTTAAAGCTATTAAAGAAGCGAAAGC  993
SPY67   951  ATGTTTCAAAAGAAGCTGTTAAAGCTATTAAAGAAGCGAAAGC  993
B514    951  ATGTTTCAAAAGAAGCTGTTAAAGCTATTAAAGAAGCGAAAGC  993
             *******************************************
```

Figure 18

```
700294    1  LGLASVAVLSLAACGNRGASKGGASGKTDLKVAMVTDTGGVDDKSFNQSA  50
12384     1  LGLASVAVLSLAACGNRGASKGGASGKTDLKVAMVTDTGGVDDKSFNQSA  50
```

```
SPY67     1  LGLASVAVLSLAACGNRGASKGGASGKTDLKVAMVTDTGGVDDKSFNQSA   50
B514      1  LGLASVAVLSLAACGNRGASKGGAAGKTDLKVAMVTDTGGVDDKSFNQSA   50
             ********************** ***************************

700294   51  WEGLQSWGKEMGLQKGTGFDYFQSTSESEYATNLDTAVSGGYQLIYGIGF  100
12384    51  WEGLQSWGKEMGLQKGTGFDYFQSTSESEYATNLDTAVSGGYQLIYGIGF  100
SPY67    51  WEGLQSWGKEMGLQKGTGFDYFQSTSESEYATNLDTAVSGGYQLIYGIGF  100
B514     51  WEGLQSWGKEMGLQKGTGFDYFQSTSESEYATNLDTAVSGGYQLIYGIGF  100
             **************************************************

700294  101  ALKDAIAKAAGDNEGVKFVIIDDIIEGKDNVASVTFADHEAAYLAGIAAA  150
12384   101  ALKDAIAKAAGDNEGVKFVIIDDIIEGKDNVASVTFADHEAAYLAGIAAA  150
SPY67   101  ALKDAIAKAAGDNEGVKFVIIDDIIEGKDNVASVTFADHEAAYLAGIAAA  150
B514    101  ALKDAIAKAAGDNEGVKFVIIDDIIEGKDNVASVTFADHEAAYLAGIAAA  150
             **************************************************

700294  151  KTTKTKTVGFVGGMEGTVITRFEKGFEAGVKSVDDTIQVKVDYAGSFGDA  200
12384   151  KTTKTKTVGFVGGMEGTVITRFEKGFEAGVKSVDDTIQVKVDYAGSFGDA  200
SPY67   151  KTTKTKTVGFVGGMEGTVITRFEKGFEAGVKSVDDTIQVKVDYAGSFGDA  200
B514    151  KTTKTKTVGFVGGMEGTVITRFEKGFEAGVKSVDDTIQVKVDYAGSFGDA  200
             **************************************************

700294  201  AKGKTIAAAQYAAGADVIYQAAGGTGAGVFNEAKAINEKRSEADKVWVIG  250
12384   201  AKGKTIAAAQYAAGADVIYQAAGGTGAGVFNEAKAINEKRSEADKVWVIG  250
SPY67   201  AKGKTIAAAQYAAGADVIYQAAGGTGAGVFNEAKAINEKRSEADKVWVIG  250
B514    201  AKGKTIAAAQYAAGADVIYQAAGGTGAGVFNEAKAINEKRSEADKVWVIG  250
             **************************************************

700294  251  VDRDQKDEGKYTSKDGKEANFVLASSIKEVGKAVQLINKQVADKKFPGGK  300
12384   251  VDRDQKDEGKYTSKDGKEANFVLASSIKEVGKAVQLINKQVADKKFPGGK  300
SPY67   251  VDRDQKDEGKYTSKDGKEANFVLASSIKEVGKAVQLINKQVADKKFPGGK  300
B514    251  VDRDQKDEGKYTSKDGKEANFVLASSIKEVGKAVQLINKQVADKKFPGGK  300
             **************************************************

700294  301  TTVYGLKDGGVEIATTNVSKEAVKAIKEAK  330
12384   301  TTVYGLKDGGVEIATTNVSKEAVKAIKEAK  330
SPY67   301  TTVYGLKDGGVEIATTNVSKEAVKAIKEAK  330
B514    301  TTVYGLKDGGVEIATTNVSKEAVKAIKEAK  330
             ******************************
```

US 7,595,057 B2

STREPTOCOCCUS PYOGENES ANTIGENS AND CORRESPONDING DNA FRAGMENTS

STATEMENT REGARDING SEQUENCE LISTING

The Sequence Listing associated with this application is provided in text format in lieu of a paper copy, and is hereby incorporated by reference into the specification. The name of the text file containing the Sequence Listing is 484112_422USPC_SEQUENCE_LISTING.txt. The text file is 52 KB, was created on Oct. 19,2007, and is being submitted electronically via EFS-Web.

FIELD OF THE INVENTION

The present invention is related to antigens, more particularly BVH-P2, BVH-P3, BVH-P4, BVH-P5, and BVH-P6 antigens of Group A *Streptococcus* (*S. pyogenes*) bacterial pathogen which may be used to prevent, diagnose and/or treat streptococcal infections.

BACKGROUND OF THE INVENTION

*Streptococci* are gram (+) bacteria which are differentiated by group specific carbohydrate antigens A through O which are found at the cell surface. *S. pyogenes* isolates are further distinguished by type-specific M protein antigens. M proteins are important virulence factors which are highly variable both in molecular weights and in sequences. Indeed, more than 80-M protein types have been identified on the basis of antigenic differences.

*S. pyogenes* is responsible for many diverse infection types, including pharyngitis, erysipelas and impetigo, scarlet fever, and invasive diseases such as bacteremia and necrotizing fasciitis. A resurgence of invasive disease in recent years has been documented in many countries, including those in North America and Europe. Although the organism is sensitive to antibiotics, the high attack rate and rapid onset of sepsis results in high morbidity and mortality.

To develop a vaccine that will protect hosts from *S. pyogenes* infection, efforts have focused on virulence factors such as the type-specific M proteins. However, the amino-terminal portion of M proteins was found to induce cross-reactive antibodies which reacted with human myocardium, tropomyosin, myosin, and vimentin, which might be implicated in autoimmune diseases. Others have used recombinant techniques to produce complex hybrid proteins containing amino-terminal peptides of M proteins from different serotypes. However, a safe vaccine containing all *S. pyogenes* serotypes will be highly complex to produce and standardize.

In addition to the serotype-specific antigens, other *S. pyogenes* proteins have generated interest as potential vaccine candidates. The C5a peptidase, which is expressed by at least *S. pyogenes* 40 serotypes, was shown to be immunogenic in mice, but its capacity to reduce the level of nasopharyngeal colonization was limited. Other investigators have also focused on the *streptococcal* pyrogenic exotoxins which appear to play an important role in pathogenesis of infection. Immunization with these proteins prevented the deadly symptoms of toxic shock, but did not prevent colonization.

The University of Oklahoma has set up a genome sequencing project for *S. pyogenes* strain M1 GAS (http://dna1.chem.ou.edu/strep.html).

Therefore there remains an unmet need for *S. pyogenes* antigens that may be used vaccine components for the prophylaxis and/or therapy of *S. pyogenes* infection.

SUMMARY OF THE INVENTION

According to one aspect, the present invention provides an isolated polynucleotide encoding a polypeptide having at least 70% identity to a second polypeptide comprising a sequence chosen from SEQ ID Nos: 2,4,6,8,10,12,14 and 16 or fragments or analogs thereof.

According to one aspect, the present invention relates to polypeptides which comprise an amino acid sequence chosen from SEQ ID Nos: 2,4,6,8,10,12,14 and 16 or fragments or analogs thereof.

In other aspects, there are provided polypeptides encoded by polynucleotides of the invention, pharmaceutical compositions, vectors comprising polynucleotides of the invention operably linked to an expression control region, as well as host cells transfected with said vectors and methods of producing polypeptides comprising culturing said host cells under conditions suitable for expression.

BRIEF DESCRIPTION OF THE DRAWINGS

In FIGS. 1, 3, 5, 7, 9, the underlined portion of the sequence represents the region coding for the leader peptide. In FIGS. 2, 4, 6, 8, 10, the underlined portion of the sequence represents the leader peptide.

FIG. 1 represents the DNA sequence of BVH-P2 gene from serotype M3 *S. pyogenes* strain ATCC12384; SEQ ID NO: 1.

FIG. 2 represents the amino acid sequence BVH-P2 polypeptide from serotype 3 *S. pyogenes* strain ATCC12384; SEQ ID NO: 2.

FIG. 3 represents the DNA sequence of BVH-P3 gene from serotype M1 *S. pyogenes* strain ATCC700294; SEQ ID NO: 3.

FIG. 4 represents the amino acid sequence BVH-P3 polypeptide from serotype M1 *S. pyogenes* strain ATCC700294; SEQ ID NO: 4.

FIG. 5 represents the DNA sequence of BVH-P4 gene from serotype M1 *S. pyogenes* strain ATCC700294; SEQ ID NO: 5.

FIG. 6 represents the amino acid sequence BVH-P4 polypeptide from serotype M1 *S. pyogenes* strain ATCC700294; SEQ ID NO: 6.

FIG. 7 represents the DNA sequence of BVH-5 gene from serotype M1 *S. pyogenes* strain ATCC700294; SEQ ID NO: 7.

FIG. 8 represents the amino acid sequence BVH-P5 polypeptide from serotype M1 *S. pyogenes* strain ATCC700294; SEQ ID NO: 8.

FIG. 9 represents the DNA sequence of BVH-P6 gene from serotype M1 *S. pyogenes* strain ATCC700294; SEQ ID NO: 9.

FIG. 10 represents the amino acid sequence BVH-P6 polypeptide from serotype M1 *S. pyogenes* strain ATCC700294; SEQ ID NO: 10.

FIG. 11 represents the DNA sequence of BVH-P4 gene from serotype M3 *S. pyogenes* strain ATCC123834; SEQ ID NO: 11.

FIG. 12 represents the amino acid sequence BVH-P4 polypeptide from serotype M3 *S. pyogenes* strain ATCC12384; SEQ ID NO: 12.

FIG. 13 represents the DNA sequence of BVH-P4 gene from serotype M6 *S. pyogenes* strain SPY67; SEQ ID NO: 13.

FIG. 14 represents the amino acid sequence BVH-P4 polypeptide from serotype M3 *S. pyogenes* strain SPY67; SEQ ID NO: 14.

FIG. 15 represents the DNA sequence of BVH-P4 gene from serotype *S. pyogenes* strain B514; SEQ ID NO: 15.

FIG. 16 represents the amino acid sequence BVH-P4 polypeptide from serotype *S. pyogenes* strain B514; SEQ ID NO: 16.

FIG. 17 depicts the comparison of the nucleotide sequences of the BVH-P4 genes from the *S. pyogens* serotype M1 ATCC700294 (SEQ ID NO: 35), serotype M3 ATCC12384 (SEQ ID NO: 36), serotype M6 SPY77 strains (SEQ ID NO: 37 and the mouse isolate B514 (SEQ ID NO: 38) by using the program CLUSTAL W from MACVECTOR sequence analysis software (version 6.5). Identical nucleotides are presented as * and differences are indicated by blank spaces.

FIG. 18 depicts the comparison of the predicted amino acid sequences of the BVH-P4 partial open reading frames from the *S. pyogenes* serotype M1 ATCC700294 (SEQ ID NO: 39), serotype M3 ATCC12384 (SEQ ID NO: 40), serotype M6 SPY77 strains (SEQ ID NO: 41) and the mouse isolate B514 (SEQ ID NO: 42) by using the program CLUSTAL W from MACVECTOR sequence analysis software (version 6.5). Underneath the alignment, there is a consensus line.

DETAILED DESCRIPTION OF THE INVENTION

The present invention provides purified and isolated DNA molecules, which encode *Streptococcal* polypeptides that can be used to prevent, treat, and/or diagnose *Streptococcal* infection.

Those skilled in the art will appreciate that the invention includes DNA molecules that encode analogs such as mutants, variants, homologues and derivatives of such polypeptides, as described herein in the present patent application. The invention also includes RNA molecules corresponding to the DNA molecules of the invention. In addition to the DNA and RNA molecules, the invention includes the corresponding polypeptides and monospecific antibodies that specifically bind to such polypeptides.

According to one aspect, the present invention provides an isolated polynucleotide encoding a polypeptide having at least 70% identity to a second polypeptide comprising a sequence chosen from SEQ ID NOs: 2, 4, 6, 8, 10, 12, 14, 16 or fragments or analogs or thereof.

According to one aspect, the present invention provides an isolated polynucleotide encoding a polypeptide having at least 80% identity to a second polypeptide comprising a sequence chosen from SEQ ID NOs: 2, 4, 6, 8, 10, 12, 14, 16 or fragments or analogs or thereof.

According to one aspect, the present invention provides an isolated polynucleotide encoding a polypeptide having at least 90% identity to a second polypeptide comprising a sequence chosen from SEQ ID NOs: 2, 4, 6, 8, 10, 12, 14, 16 or fragments or analogs or thereof.

According to one aspect, the present invention provides an isolated polynucleotide encoding a polypeptide having at least 95% identity to a second polypeptide comprising a sequence chosen from SEQ ID NOs: 2, 4, 6, 8, 10, 12, 14, 16 or fragments or analogs or thereof.

According to one aspect, the present invention provides a polynucleotide encoding a polypeptide comprising a sequence chosen from SEQ ID NOs: 2, 4, 6, 8, 10, 12, 14 or 16 or fragments or analogs or thereof.

According to one aspect, the present invention provides a polynucleotide encoding a polypeptide capable of generating antibodies having binding specificity for a polypeptide having a sequence chosen from SEQ ID NOs: 2, 4, 6, 8, 10, 12, 14 or 16 or fragments or analogs or thereof.

According to one aspect, the present invention provides a polynucleotide encoding an epitope bearing portion of a polypeptide having a sequence chosen from: SEQ ID NOs: 2, 4, 6, 8, 10, 12, 14 or 16 or fragments or analogs or thereof.

According to one aspect, the present invention relates to epitope bearing portions of a polypeptide having a sequence chosen from SEQ ID NOs: 2, 4, 6, 8, 10, 12, 14 or 16 or fragments or analogs or thereof.

According to one aspect, the present invention provides an isolated polynucleotide encoding a polypeptide having at least 70% identity to a second polypeptide comprising a sequence chosen from SEQ ID NOs: 2, 4, 6, 8, 10, 12, 14 or 16.

According to one aspect, the present invention provides an isolated polynucleotide encoding a polypeptide having at least 80% identity to a second polypeptide comprising a sequence chosen from SEQ ID NOs: 2, 4, 6, 8, 10, 12, 14 or 16.

According to one aspect, the present invention provides an isolated polynucleotide encoding a polypeptide having at least 90% identity to a second polypeptide comprising a sequence chosen from SEQ ID NOs: 2, 4, 6, 8, 10, 12, 14 or 16.

According to one aspect, the present invention provides an isolated polynucleotide encoding a polypeptide having at least 95% identity to a second polypeptide comprising a sequence chosen from SEQ ID NOs: 2, 4, 6, 8, 10, 12, 14 or 16.

According to one aspect, the present invention provides a polynucleotide encoding a polypeptide comprising a sequence chosen from SEQ ID NOs: 2, 4, 6, 8, 10, 12, 14 or 16 or fragments or analogs or thereof.

According to one aspect, the present invention provides a polynucleotide encoding a polypeptide capable of generating antibodies having binding specificity for a polypeptide having a sequence chosen from SEQ ID NOs: 2, 4, 6, 8, 10, 12, 14 or 16.

According to one aspect, the present invention provides a polynucleotide encoding an epitope bearing portion of a polypeptide having a sequence chosen from: SEQ ID NOs: 2, 4, 6, 8, 10, 12, 14 or 16.

According to one aspect, the present invention relates to epitope bearing portions of a polypeptide having a sequence chosen from SEQ ID NOs: 2, 4, 6, 8, 10, 12, 14 or 16.

In accordance with the present invention, all polynucleotides encoding polypeptides are within the scope of the present invention.

According to one aspect, the present invention relates to polypeptides having at least 70% identity to a second polypeptide having an amino acid sequence chosen from: SEQ ID NOs: 2, 4, 6, 8, 10, 12, 14, 16 or fragments or analogs thereof.

According to one aspect, the present invention relates to polypeptides having at least 95% identity to a second polypeptide having an amino acid sequence chosen from: SEQ ID NOs: 2, 4, 6, 8, 10, 12, 14, 16 or fragments or analogs thereof.

According to one aspect, the present invention relates to polypeptides characterized by the amino acid sequence comprising sequences from SEQ ID NOs: 2,4,6,8,10,12,14,16 or fragments or analogs thereof.

According to one aspect, the present invention relates to polypeptides capable of generating antibodies having binding specificity for a polypeptide having a sequence chosen from SEQ ID NOs: 2, 4, 6, 8, 10, 12, 14, 16 or fragments or analogs thereof.

According to one aspect, the present invention relates to epitope bearing portions of a polypeptide having a sequence chosen from SEQ ID NOs: 2, 4, 6, 8, 10, 12, 14, 16 or fragments or analogs thereof.

According to one aspect, the present invention relates to polypeptides having at least 70% identity to a second polypeptide having an amino acid sequence chosen from: SEQ ID NOs: 2, 4, 6, 8, 10, 12, 14, 16,.

According to one aspect, the present invention relates to polypeptides having at least 95% identity to a second polypeptide having an amino acid sequence chosen from: SEQ ID NOs: 2, 4, 6, 8, 10, 12, 14, 16,.

According to one aspect, the present invention relates to polypeptides characterized by the amino acid sequence comprising sequences from SEQ ID NOs: 2,4,6,8,10,12,14,16.

According to one aspect, the present invention relates to polypeptides capable of generating antibodies having binding specificity for a polypeptide having a sequence chosen from SEQ ID NOs: 2, 4, 6, 8, 10, 12, 14, 16.

According to one aspect, the present invention relates to epitope bearing portions of a polypeptide having a sequence chosen from SEQ ID NOs: 2, 4, 6, 8, 10, 12, 14, 16.

In a further embodiment, the polypeptides in accordance with the present invention are antigenic.

In a further embodiment, the polypeptides in accordance with the present invention are immunogenic.

In a further embodiment, the polypeptides in accordance with the present invention can elicit an immune response in a host.

In a further embodiment, the present invention also relates to polypeptides which are able to raise antibodies having binding specificity to the polypeptides of the present invention as defined above.

An antibody that "has binding specificity" is an antibody that recognizes and binds the selected polypeptide but which does not substantially recognize and bind other molecules in a sample, e.g., a biological sample, which naturally includes the selected peptide. Specific binding can be measured using an ELISA assay in which the selected polypeptide is used as an antigen.

In accordance with the present invention, "protection" in the biological studies is defined by a significant increase in the survival curve, rate or period. Statistical analysis using the Log rank test to compare survival curves, and Fisher exact test to compare survival rates and numbers of days to death, respectively, might be useful to calculate P values and determine whether the difference between the two groups is statistically significant. P values of 0.05 are regarded as not significant.

In accordance with the present invention, there is provided a consensus nucleotide sequence for BVH-P4 depicted in FIG. 17. As can be seen by the alignement, the polynucleotide encoding the polypeptide of the invention is well conserved. Without restricting the scope of the invention, the following table A shows the possible modifications:

| Position on alignement in FIG. 17 | Possible nucleotide |
|---|---|
| 74 | G or T |
| 130 | C or T |
| 253 | C or T |
| 274 | G or A |
| 412 | C or T |
| 445 | A or G |
| 841 | T or C |
| 868 | G or A |
| 917 | C or T |

In accordance with the present invention, there is provided a consensus amino acid sequence for BVH-P4 depicted in FIG. 18. As can be seen by the alignement, the polypeptide of the invention is well conserved. Without restricting the scope of the invention, the following table B shows the possible modifications:

| Position on alignement in FIG. 18 | Possible amino acid |
|---|---|
| 25 | S or A |

In an additional aspect of the invention there are provided antigenic/immunogenic fragments of the polypeptides of the invention, or of analogs thereof.

The fragments of the present invention should include one or more such epitopic regions or be sufficiently similar to such regions to retain their antigenic/immunogenic properties. Thus, for fragments according to the present invention the degree of identity is perhaps irrelevant, since they may be 100% identical to a particular part of a polypeptide or analog thereof as described herein. The present invention further provides fragments having at least 10 contiguous amino acid residues from the polypeptide sequences of the present invention. In one embodiment, at least 15 contiguous amino acid residues. In one embodiment, at least 20 contiguous amino acid residues.

The skilled person will appreciate that analogs of the polypeptides of the invention will also find use in the context of the present invention, i.e. as antigenic/immunogenic material. Thus, for instance proteins or polypeptides which include one or more additions, deletions, substitutions or the like are encompassed by the present invention.

These substitutions are those having a minimal influence on the secondary structure and hydropathic nature of the polypeptide. Preferred substitutions are those known in the art as conserved, i.e. the substituted residues share physical or chemical properties such as hydrophobicity, size, charge or functional groups. These include substitutions such as those described by Dayhoff, M. in Atlas of Protein Sequence and Structure 5, 1978 and by Argos, P. in EMBO J. 8, 779-785, 1989. For example, amino acids, either natural or unnatural, belonging to one of the following groups represent conservative changes:

ala, pro, gly, gln, asn, ser, thr, val;
cys, ser, tyr, thr;
val, ile, leu, met, ala, phe;
lys, arg, orn, his;
and phe, tyr, trp, his.

The preferred substitutions also include substitutions of D-enantiomers for the corresponding L-amino acids.

The percentage of homology is defined as the sum of the percentage of identity plus the percentage of similarity or conservation of amino acid type.

In an alternative approach, the analogs could be fusion proteins, incorporating moieties which render purification easier, for example by effectively tagging the desired polypeptide. It may be necessary to remove the "tag" or it may be the case that the fusion polypeptide itself retains sufficient antigenicity to be useful.

Thus, what is important for analogs, derivatives and fragments is that they possess at least a degree of the antigenicity/immunogenic of the protein or polypeptide from which they are derived.

As used herein, "fragments", "analogs" or "derivatives" of the polypeptides of the invention include those polypeptides in which one or more of the amino acid residues are substituted with a conserved or non-conserved amino acid residue (preferably conserved) and which may be natural or unnatural.

In one embodiment, analogs of polypeptides of the invention will have about 70% identity with those sequences illustrated in the figures or fragments thereof. That is, 70% of the residues are the same. In a further embodiment, polypeptides will have greater than 75% homology. In a further embodiment, polypeptides will have greater than 80% homology. In a further embodiment, polypeptides will have greater than 85% homology. In a further embodiment, polypeptides will have greater than 90% homology. In a further embodiment, polypeptides will have greater than 95% homology. In a further embodiment, polypeptides will have greater than 99% homology. In a further embodiment, analogs of polypeptides of the invention will have fewer than about 20 amino acid residue substitutions, modifications or deletions and more preferably less than 10.

In a further embodiment, polypeptides will have greater than 70% homology. In a further embodiment, polypeptides will have greater than 75% homology. In a further embodiment, polypeptides will have greater than 80% homology. In a further embodiment, polypeptides will have greater than 85% homology. In a further embodiment, polypeptides will have greater than 90% homology. In a further embodiment, polypeptides will have greater than 95% homology. In a further embodiment, polypeptides will have greater than 99% homology. In a further embodiment, derivatives and analogs of polypeptides of the invention will have less than about 20 amino acid residue substitutions, modifications or deletions and more preferably less than 10. Preferred substitutions are those known in the art as conserved i.e. the substituted residues share physical or chemical properties such as hydrophobicity, size, charge or functional groups.

One can use a program such as the CLUSTAL program to compare amino acid sequences. This program compares amino acid sequences and finds the optimal alignment by inserting spaces in either sequence as appropriate. It is possible to calculate amino acid identity or similarity (identity plus conservation of amino acid type) for an optimal alignment. A program like BLASTx will align the longest stretch of similar sequences and assign a value to the fit. It is thus possible to obtain a comparison where several regions of similarity are found, each having a different score. Both types of identity analysis are contemplated in the present invention.

In an additional aspect of the invention there are provided antigenic/immunogenic fragments of the polypeptides of the invention, or of analogs thereof.

For fragments of the polypeptides described herein, or of analogs thereof, the situation is slightly different from native protein. It is well known that it is possible to screen an antigenic polypeptide to identify epitopic regions, i.e. those regions which are responsible for the polypeptide's antigenicity or immunogenicity. Methods for carrying out such screening are well known in the art. Thus, the fragments of the present invention should include one or more such epitopic regions or be sufficiently similar to such regions to retain their antigenic/immunogenic properties. Thus, for fragments according to the present invention the degree of identity is perhaps irrelevant, since they may be 100% identical to a particular part of a polypeptide, analog as described herein.

Also included are polypeptides which have fused thereto other compounds which alter the polypeptides biological or pharmacological properties i.e. polyethylene glycol (PEG) to increase half-life; leader or secretory amino acid sequences for ease of purification; prepro- and pro-sequences; and (poly)saccharides.

Furthermore, in those situations where amino acid regions are found to be polymorphic, it may be desirable to vary one or more particular amino acids to more effectively mimic the different epitopes of the different *streptococcus* strains.

Moreover, the polypeptides of the present invention can be modified by terminal —NH$_2$ acylation (eg. by acetylation, or thioglycolic acid amidation, terminal carboxy amidation, e.g. with ammonia or methylamine) to provide stability, increased hydrophobicity for linking or binding to a support or other molecule.

Also contemplated are hetero and homo polypeptide multimers of the polypeptide fragments and analogues. These polymeric forms include, for example, one or more polypeptides that have been cross-linked with cross-linkers such as avidin/biotin, gluteraldehyde or dimethylsuperimidate. Such polymeric forms also include polypeptides containing two or more tandem or inverted contiguous sequences, produced from multicistronic mRNAs generated by recombinant DNA technology. In a further embodiment, the present invention also relates to chimeric polypeptides which comprise one or more polypeptides or fragments or analogs thereof as defined in the figures of the present application.

In a further embodiment, the present invention also relates to chimeric polypeptides comprising two or more polypeptides having a sequence chosen from SEQ ID NOs: 2, 4, 6, 8, 10, 12, 14, 16 or fragments or analogs thereof; provided that the polypeptides are linked as to formed a chimeric polypeptide.

In a further embodiment, the present invention also relates to chimeric polypeptides comprising two or more polypeptides having a sequence chosen from SEQ ID NOs: 2, 4, 6, 8, 10, 12, 14 or 16 provided that the polypeptides are linked as to formed a chimeric polypeptide.

In order to achieve the formation of antigenic polymers (i.e. synthetic multimers), polypeptides may be utilized having bishaloacetyl groups, nitroarylhalides, or the like, where the reagents being specific for thio groups. Therefore, the link between two mercapto groups of the different polypeptides may be a single bond or may be composed of a linking group of at least two, typically at least four, and not more than 16, but usually not more than about 14 carbon atoms.

In a particular embodiment, polypeptide fragments and analogs of the invention do not contain a starting residue, such as methionine (Met) or valine (Val).

Preferably, polypeptides will not incorporate a leader or secretory sequence (signal sequence). The signal portion of a polypeptide of the invention may be determined according to established molecular biological techniques. The polypeptide of interest may be isolated from a *streptococcal* culture and subsequently sequenced to determine the initial residue of the mature protein and therefore the sequence of the mature polypeptide.

It is understood that polypeptides can be produced and/or used without their start codon (methionine or valine) and/or without their leader peptide to favor production and purification of recombinant polypeptides. It is known that cloning genes without sequences encoding leader peptides will restrict the polypeptides to the cytoplasm of *E. coli* and will facilitate their recovery (Glick, B. R. and Pasternak, J. J. (1998) Manipulation of gene expression in prokaryotes. In "Molecular biotechnology: Principles and applications of recombinant DNA", 2nd edition, ASM Press, Washington D.C., p.109-143).

The polypeptides may be expressed with or without a leader or secretion sequence. In the former case, the leader may be removed using post-translational processing (see U.S. Pat. Nos. 4,431,739, 4,425,437 and 4,338,397 incorporated herein by reference) or be chemically removed subsequent to purifying the expressed polypeptide.

According to another aspect of the invention, there are also provided (i) a composition of matter containing a polypeptide of the invention, together with a carrier, diluent or adjuvant; (ii) a pharmaceutical composition comprising a polypeptide of the invention and a carrier, diluent or adjuvant; (iii) a vaccine comprising a polypeptide of the invention and a carrier, diluent or adjuvant; (iv) a method for inducing an immune response against *Streptococcus*, in a host, by administering to the host, an immunogenically effective amount of a polypeptide of the invention to elicit an immune response, e.g., a protective immune response to *Streptococcus*; and particularly, (v) a method for preventing and/or treating a *Streptococcus* infection, by administering a prophylactic or therapeutic amount of a polypeptide of the invention to a host in need.

Before immunization, the polypeptides of the invention can also be coupled or conjugated to carrier proteins such as tetanus toxin, diphtheria toxin, hepatitis B virus surface antigen, poliomyelitis virus VP1 antigen or any other viral or bacterial toxin or antigen or any suitable proteins to stimulate the development of a stronger immune response. This coupling or conjugation can be done chemically or genetically. A more detailed description of peptide-carrier conjugation is available in Van Regenmortel, M. H. V., Briand J. P., Muller S., Plaué S., <<Synthetic Polypeptides as antigens>> in Laboratory Techniques in Biochemistry and Molecular Biology, Vol.19 (ed.) Burdou, R. H. & Van Knippenberg P. H. (1988), Elsevier New York.

According to another aspect, there are provided pharmaceutical compositions comprising one or more *Streptococcal* polypeptides of the invention in a mixture with a pharmaceutically acceptable adjuvant. Suitable adjuvants include (1) oil-in-water emulsion formulations such as MF59™, SAF™, Ribi™; (2) Freund's complete or incomplete adjuvant; (3) salts i.e. $AlK(SO_4)_2$, $AlNa(SO_4)_2$, $AlNH_4(SO_4)_2$, $Al(OH)_3$, $AlPO_4$, silica, kaolin; (4) saponin derivatives such as Stimulon™ or particles generated therefrom such as ISCOMs (immunostimulating complexes); (5) cytokines such as interleukins, interferons, macrophage colony stimulating factor (M-CSF), tumor necrosis factor (TNF); (6) other substances such as carbon polynucleotides (e.g. poly IC and poly AU), detoxified cholera toxin (CTB), and *E. coli* heat labile toxin for induction of mucosal immunity. A more detailed description of adjuvants is available in a review by M.Z.I Khan et al. in Pharmaceutical Research, vol. 11, No. 1 (1994) pp2-11, and also in another review by Gupta et al., in Vaccine, Vol. 13, No. 14, pp1263-1276 (1995) and in WO 99/24578. Preferred adjuvants include QuilA™ (an adjuvant containing saponins from the bark of *Quillaja saponaria*), QS2™, Alhydrogel™ (aluminum hydroxide (hydrated aluminum) and Adjuphos™ (aluminum phosphate).

In a further embodiment, there is provided a method of manufacturing a pharmaceutical composition comprising admixing a polypeptide of the invention with a pharmaceutically acceptable diluent, excipient or adjuvant.

In a further aspect, the invention provides a method for prophylactic or therapeutic treatment of *Streptopcoccal* bacterial infection in a host susceptible to *Streptococcal* infection comprising administering to a host a therapeutic or prophylactic amount of a composition of the invention.

Pharmaceutical compositions of the invention may be administered parenterally by injection, rapid infusion, nasopharyngeal absorption, dermoabsorption, or bucal or oral. Pharmaceutically acceptable carriers also include tetanus toxoid.

Pharmaceutical compositions of the invention are used for the treatment or prophylaxis of *streptococcal* infection and/or diseases and symptoms mediated by *streptococcal* infection as described in P. R. Murray (Ed, in chief), E. J. Baron, M. A. Pfaller, F. C. Tenover and R. H. Yolken. Manual of Clinical Microbiology, ASM Press, Washington, D.C. sixth edition, 1995, 1482p which are herein incorporated by reference. In one embodiment, pharmaceutical compositions of the present invention are used for the treatment or prophylaxis of pharyngitis, erysipelas and impetigo, scarlet fever, and invasive diseases such as bacteremia and necrotizing fasciitis and also toxic shock. In one embodiment, pharmaceutical compositions of the invention are used for the treatment or prophylaxis of *streptococcus* infection and/or diseases and symptoms mediated by *streptococcus* infection, in particular group A *streptococcus* (*S. pyogenes*), group B *streptococcus* (GBS or *S. agalactiae*), *S. pneumoniae*, *S. dysgalactiae*, *S. uberis*, *S. nocardia* as well as *Staphylococcus aureus*. In a further embodiment, the *streptococcus* infection is *Streptococcus pyogenes*.

In a particular embodiment, pharmaceutical compositions are administered to those host at risk of *streptococcus* infection such as infants, elderly and immunocompromised hosts.

According to a further aspect, the *streptococcal* polypeptides of the invention may be used in a kit comprising the polypeptides of the invention for detection or diagnosis of *streptococcal* infection.

As used in the present application, the term "host" include mammals. In a further embodiment, the mammal is human.

Pharmaceutical compositions are preferably in unit dosage form of about 0.001 to 100 µg/kg (antigen/body weight) and more preferably 0.01 to 10 µg/kg and most preferably 0.1 to 1 µg/kg 1 to 3 times with an interval of about 1 to 6 week intervals between immunizations.

Pharmaceutical compositions are preferably in unit dosage form of about 0.1 µg to 10 mg and more preferably 1 µg to 1 mg and most preferably 10 to 100 µg 1 to 3 times with an interval of about 1 to 6 week intervals between immunizations.

In one embodiment, polynucleotides are those illustrated in SEQ ID Nos: 1, 3, 5, 7, 9, 11, 13, 15 which may include the open reading frames (ORF), encoding the polypeptides of the invention.

It will be appreciated that the polynucleotide sequences illustrated in the figures may be altered with degenerate codons yet still encode the polypeptides of the invention. Accordingly the present invention further provides polynucleotides which hybridize to the polynucleotide sequences herein above described (or the complement sequences thereof) having 50% identity between sequences. In one embodiment, at least 70% identity between sequences. In one embodiment, at least 75% identity between sequences. In one embodiment, at least 80% identity between sequences. In one embodiment, at least 85% identity between sequences. In one embodiment, at least 90% identity between sequences. In a further embodiment, polynucleotides are hybridizable under stringent conditions i.e. having at least 95% identity. In a further embodiment, more than 97% identity.

Suitable stringent conditions for hybridation can be readily determined by one of skilled in the art (see for example Sambrook et al., (1989) Molecular cloning: A Laboratory Manual, $2^{nd}$ ed, Cold Spring Harbor, N.Y.; Current Protocols in Molecular Biology, (1999) Edited by Ausubel F. M. et al., John Wiley & Sons, Inc., N.Y.).

In a further embodiment, the present invention provides polynucleotides that hybridize under stringent conditions to either
(a) a DNA sequence encoding a polypeptide or
(b) the complement of a DNA sequence encoding a polypeptide;

wherein said polypeptide comprises SEQ ID NO: 2, 4, 6, 8, 10, 12, 14 or 16 or fragments or analogs thereof.

In a further embodiment, the present invention provides polynucleotides that hybridize under stringent conditions to either
(a) a DNA sequence encoding a polypeptide or
(b) the complement of a DNA sequence encoding a polypeptide;

wherein said polypeptide comprises SEQ ID NO: 2, 4, 6, 8, 10, 12, 14 or 16.

In a further embodiment, the present invention provides polynucleotides that hybridize under stringent conditions to either
(a) a DNA sequence encoding a polypeptide or
(b) the complement of a DNA sequence encoding a polypeptide;

wherein said polypeptide comprises at least 10 contiguous amino acid residues from a polypeptide comprising SEQ ID NO: 2, 4, 6, 8, 10, 12, 14 or 16 or fragments or analogs thereof.

In a further embodiment, the present invention provides polynucleotides that hybridize under stringent conditions to either
(a) a DNA sequence encoding a polypeptide or
(b) the complement of a DNA sequence encoding a polypeptide;

wherein said polypeptide comprises at least 10 contiguous amino acid residues from a polypeptide comprising SEQ ID NO: 2, 4, 6, 8, 10, 12, 14 or 16.

In a further embodiment, polynucleotides are those illustrated in SEQ ID NOs: 1, 3, 5, 7, 9, 11, 13, 15 encoding polypeptides of the invention.

As will be readily appreciated by one skilled in the art, polynucleotides include both DNA and RNA.

The present invention also includes polynucleotides complementary to the polynucleotides described in the present application.

In a further aspect, polynucleotides encoding polypeptides of the invention, or fragments, analogs or derivatives thereof, may be used in a DNA immunization method. That is, they can be incorporated into a vector which is replicable and expressible upon injection thereby producing the antigenic polypeptide in vivo. For example polynucleotides may be incorporated into a plasmid vector under the control of the CMV promoter which is functional in eukaryotic cells. Preferably the vector is injected intramuscularly.

According to another aspect, there is provided a process for producing polypeptides of the invention by recombinant techniques by expressing a polynucleotide encoding said polypeptide in a host cell and recovering the expressed polypeptide product. Alternatively, the polypeptides can be produced according to established synthetic chemical techniques i.e. solution phase or solid phase synthesis of oligopeptides which are ligated to produce the full polypeptide (block ligation).

General methods for obtention and evaluation of polynucleotides and polypeptides are described in the following references: Sambrook et al, Molecular Cloning: A Laboratory Manual, 2nd ed, Cold Spring Harbor, N.Y., 1989; Current Protocols in Molecular Biology, Edited by Ausubel F. M. et al., John Wiley and Sons, Inc. New York; PCR Cloning Protocols, from Molecular Cloning to Genetic Engineering, Edited by White B. A., Humana Press, Totowa, N.J., 1997, 490 pages; Protein Purification, Principles and Practices, Scopes R. K., Springer-Verlag, New York, 3rd Edition, 1993, 380 pages; Current Protocols in Immunology, Edited by Coligan J. E. et al., John Wiley & Sons Inc., New York.

For recombinant production, host cells are transfected with vectors which encode the polypeptide, and then cultured in a nutrient media modified as appropriate for activating promoters, selecting transformants or amplifying the genes. Suitable vectors are those that are viable and replicable in the chosen host and include chromosomal, non-chromosomal and synthetic DNA, sequences, e.g., bacterial plasmids, phage DNA, baculovirus, yeast plasmids, vectors derived from combinations of plasmids and phage DNA. The polypeptide sequence may be incorporated in the vector at the appropriate site using restriction enzymes such that it is operably linked to an expression control region comprising a promoter, ribosome binding site (consensus region or Shine-Dalgarno sequence), and optionally an operator (control element). One can select individual components of the expression control region that are appropriate for a given host and vector according to established molecular biology principles (Sambrook et al, Molecular Cloning: A Laboratory Manual, 2nd ed, Cold Spring Harbor, N.Y., 1989; Current Protocols in Molecular Biology, Edited by Ausubel F. M. et al., John Wiley and Sons, Inc. New York). Suitable promoters include but are not limited to LTR or SV40 promoter, *E. coli* lac, tac or trp promoters and the phage lambda $P_L$ promoter. Vectors will preferably incorporate an origin of replication as well as selection markers e.g., an ampicillin resistance gene. Suitable bacterial vectors include pET, pQE70, pQE60, pQE-9, pD10 PHAGESCRIPT, psiX174, pBLUESCRIPT SK, pbsks, pNH8A, pNH16a, pNH18A, pNH46A, ptrc99a, pKK223-3, pKK233-3, pDR540, pRIT5 and eukaryotic vectors pBLUEBACIII, pWLNEO, pSV2CAT, pOG44, pXT1, pSG, pSVK3, PBPV, pMSG and pSVL. Host cells may be bacterial (e.g., *E. coli, Bacillus subtilis, Streptomyces*); fungal (e.g., *Aspergillus niger, Aspergillus nidulins*); yeast (e.g., *Saccharomyces*) or eukaryotic (e.g., CHO, COS).

Upon expression of the polypeptide in culture, cells are typically harvested by centrifugation then disrupted by physical or chemical means (if the expressed polypeptide is not secreted into the media) and the resulting crude extract retained to isolate the polypeptide of interest. Purification of the polypeptide from culture media or lysate may be achieved by established techniques depending on the properties of the polypeptide i.e. using ammonium sulfate or ethanol precipitation, acid extraction, anion or cation exchange chromatography, phosphocellulose chromatography, hydrophobic interaction chromatography, hydroxylapatite chromatography and lectin chromatography. Final purification may be achieved using HPLC.

According to a further aspect, the *streptococcal* polypeptides of the invention may be used in a diagnostic test for *streptococcus* infection, in particular *Streptococcus pyogenes* infection. Several diagnostic methods are possible, for example detecting *streptococcus* organism in a biological sample, the following procedure may be followed:

a) obtaining a biological sample from a host;
b) incubating an antibody or fragment thereof reactive with a *streptococcus* polypeptide of the invention with the biological sample to form a mixture; and
c) detecting specifically bound antibody or bound fragment in the mixture which indicates the presence of *streptococcus*.

Alternatively, a method for the detection of antibody specific to a *streptococcus* antigen in a biological sample containing or suspected of containing said antibody may be performed as follows:
a) obtaining a biological sample from a host;
b) incubating one or more *streptococcus* polypeptides of the invention or fragments thereof with the biological sample to form a mixture; and
c) detecting specifically bound antigen or bound fragment in the mixture which indicates the presence of antibody specific to *streptococcus*.

One of skill in the art will recognize that this diagnostic test may take several forms, including an immunological test such as an enzyme-linked immunosorbent assay (ELISA), a radioimmunoassay or a latex agglutination assay, essentially to determine whether antibodies specific for the protein are present in an organism.

The DNA sequences encoding polypeptides of the invention may also be used to design DNA probes for use in detecting the presence of *streptococcus* in a biological sample suspected of containing such bacteria. The detection method of this invention comprises:
a) obtaining the biological sample from a host;
b) incubating one or more DNA probes having a DNA sequence encoding a polypeptide of the invention or fragments thereof with the biological sample to form a mixture; and
c) detecting specifically bound DNA probe in the mixture which indicates the presence of *streptococcus* bacteria.

The DNA probes of this invention may also be used for detecting circulating *streptococcus* i.e. *Streptococcus pyogenes* nucleic acids in a sample, for example using a polymerase chain reaction, as a method of diagnosing *streptococcus* infections. The probe may be synthesized using conventional techniques and may be immobilized on a solid phase, or may be labelled with a detectable label. A preferred DNA probe for this application is an oligomer having a sequence complementary to at least about 6 contiguous nucleotides of the *Streptococcus pyogenes* polypeptides of the invention.

Another diagnostic method for the detection of *streptococcus* in a host comprises:
a) labelling an antibody reactive with a polypeptide of the invention or fragment thereof with a detectable label;
b) administering the labelled antibody or labelled fragment to the host; and
c) detecting specifically bound labelled antibody or labelled fragment in the host which indicates the presence of *streptococcus*.

A further aspect of the invention is the use of the *streptococcus* polypeptides of the invention as immunogens for the production of specific antibodies for the diagnosis and in particular the treatment of *streptococcus* infection. Suitable antibodies may be determined using appropriate screening methods, for example by measuring the ability of a particular antibody to passively protect against *streptococcus* infection in a test model. One example of an animal model is the mouse model described in the examples herein. The antibody may be a whole antibody or an antigen-binding fragment thereof and may belong to any immunoglobulin class. The antibody or fragment may be of animal origin, specifically of mammalian origin and more specifically of murine, rat or human origin. It may be a natural antibody or a fragment thereof, or if desired, a recombinant antibody or antibody fragment. The term recombinant antibody or antibody fragment means antibody or antibody fragment which was produced using molecular biology techniques. The antibody or antibody fragments may be polyclonal, or preferably monoclonal. It may be specific for a number of epitopes associated with the *Streptococcus pyogenes* polypeptides but is preferably specific for one.

A further aspect of the invention is the use of the antibodies directed to the polypeptides of the invention for passive immunization. One could use the antibodies described in the present application. Suitable antibodies may be determined using appropriate screening methods, for example by measuring the ability of a particular antibody to passively protect against *streptococcal* infection in a test model. One example of an animal model is the mouse model described in the examples herein. The antibody may be a whole antibody or an antigen-binding fragment thereof and may belong to any immunoglobulin class. The antibody or fragment may be of animal origin, specifically of mammalian origin and more specifically of murine, rat or human origin. It may be a natural antibody or a fragment thereof, or if desired, a recombinant antibody or antibody fragment. The term recombinant antibody or antibody fragment means antibody or antibody fragment which was produced using molecular biology techniques. The antibody or antibody fragments may be polyclonal, or preferably monoclonal. It may be specific for a number of epitopes associated with the *streptococcal* polypeptides but is preferably specific for one.

According to one aspect, the present invention provides the use of an antibody for treatment and/or prophylaxis of *streptococcal* infections.

Unless otherwise defined, all technical and scientific terms used herein have the same meaning as commonly understood by one of ordinary skill in the art to which this invention belongs. All publications, patent applications, patents, and other references mentioned herein are incorporated by reference in their entirety. In case of conflict, the present specification, including definitions, will control. In addition, the materials, methods, and examples are illustrative only and not intended to be limiting.

EXAMPLE 1

This Example Illustrates the Cloning and Molecular Characteristics of BVH-P2 Gene and Corresponding Polypeptide The coding region of *S. pyogenes* BVH-P2 gene (SEQ ID NO: 1) was amplified by PCR (ROBOCYCLER Gradient 96 Temperature cycler, STRATAGENE, LaJolla, CA) from genomic DNA of serotype M3 *S. pyogenes* strain ATCC12384 using the following oligonuceotide primers that contained base extensions for the addition of restriction sites NdeI (CATATG) and XhoI (CTCGAG): DMAR124 and DMAR125, which are presented in Table 1. PCR products were purified from agarose gel using a QIAQUICK gel extraction kit from QIAgen following the manufacturer's Instructions (Chatsworth, CA), and digested with NdeI and XhoI (PHARMACIA Canada Inc, Baie d'Urfe, Canada). The pET-21b(+) vector (NOVAGEN, Madison, WI) was digested with NdeI and XhoI and purified from agarose gel using a QIAQUICK gel extraction kit from QIAGEN (Chatsworth, CA). The NdeI-XhoI PCR products were ligated to the NdeI-XhoI pET-21b(+) expression vector. The ligated products were transformed into *E. coli* strain DH5α [φ80dlacZΔM15 Δ(lacZYA-argF)U169 endA1 recA1 hsdR17($r_K^-$–$m_K^-$+) deoR thi-1 supE44 λ⁻gyrA96 relA1] (Gibco BRL, Gaithersburg, MD) according to the method of Simanis (Hanahan, D. DNA Cloning, 1985, D. M. Glover (ed), pp. 109-135). Recombinant pET-21b(+) plasmid (rpET21b(+)) containing BVH-P2 gene was purified using a QIAGEN plasmid kit (Chatsworth, CA) and DNA insert was sequenced (Taq Dye Deoxy Terminator Cycle Sequencing kit, ABI, Foster City, CA).

TABLE 1

Oligonucleotide primers used for PCR amplifications of S. pyogenes genes

| Genes | Primers I.D. | Restriction site | Vector | Sequence | SEQ ID No |
|---|---|---|---|---|---|
| BVH-P2 | DMAR124 | NdeI | pET21b | 5'-CGGAGAGAACATATG AAAAAGACATTAAC-3' | 17 |
| BVH-P2 | DMAR125 | XhoI | pET21b | 5'-GGGCTCGAGCTGAAA CAGTCCCTTAAAG-3' | 18 |
| BVH-P2 | DMAR507 | BamHI | pCMV-GH | 5'-GAGCGGATCCTGAAC AAAGTAG-3' | 19 |
| BVH-P2 | DMAR508 | SalI | pCMV-GH | 5'-GGGGTCGACCTGAAA CAGTCCCTTAAAG-3' | 20 |
| BVH-P3 | DMAR188 | NdeI | pET21b | 5'-GATGGGAAAGCATAT GAGCCTCATTTTG-3' | 21 |
| BVH-P3 | DMAR189 | XhoI | pET21b | 5'-GGCTCGAGTTTTGCT AGACCTTCAG-3' | 22 |
| BVH-P4 | DMAR192 | NdeI | pET21b | 5'-GGGTTCATACATATG AACAAGAAATTTATTGG-3' | 23 |
| BVH-P4 | DMAR193 | XhoI | pET21b | 5'-GGCTCGAGTTTTTCA GGAACTTTAATG-3' | 24 |
| BVH-P4 | DMAR509 | BamHI | pCMV-GH | 5'-GTTTGGATCCTTGTG GTAATCGTGG-3' | 25 |
| BVH-P4 | DMAR510 | SalI | pCMV-GH | 5'-GGGTCGACTTTTTCA GGAACTTTAATG-3' | 26 |
| BVH-P5 | DMAR200 | NdeI | pET21b | 5'-GGTTCATTTTCATAT GAACAAAAAAGTAATG-3' | 27 |
| BVH-P5 | DMAR201 | XhoI | pET21b | 5'-GGCTCGAGGTTTTCA GGAACTGTGATGG-3' | 28 |
| BVH-P5 | DMAR511 | BamHI | pCMV-GH | 5'-GCGGATCCTACCAAT AACTCCGCTAAACA-3' | 29 |
| BVH-P5 | DMAR512 | SalI | pCMV-GH | 5'-CAGGTCGACTTTTCA GGAACTGTGATGGTTC-3' | 30 |
| BVH-P6 | DMAR235 | NdeI | pET21b | 5'-GGATAGTTTTCATAT GAATCAAGAGATTAG-3' | 31 |
| BVH-P6 | DMAR236 | XhoI | pET21b | 5'-CCCTCGAGATTGGTC TGATTCCAACTATC-3' | 32 |
| BVH-P6 | DMAR513 | BamHI | pCMV-GH | 5'-TTTGGATCCTAATCA AGAGATTAGATATTC-3' | 33 |
| BVH-P6 | DMAR514 | SalI | pCMV-GH | 5'-CCGTCGACATTGGTC TGATTCCAACTATC-3' | 34 |

It was determined that the open reading frame (ORF) which codes for BVH-P2 contains 633-bp and encodes a 210 amino acid residues polypeptide with a predicted pI of 6.40 and a predicted molecular mass of 24,611.78 Da. Analysis of the predicted amino acid residues sequence (SEQ ID NO:2) using the Spscan software (Wisconsin Sequence Analysis Package; Genetics Computer Group) suggested the existence of a 22 amino acid residues signal peptide (MKKTLTLLLA-LFAIGVTSSVRA)(SEQ ID NO: 43), which ends with a cleavage site situated between an alanine and a glutamic acid residue.

To confirm the presence by PCR amplification of BVH-P2 (SEQ ID NO:1) gene, the following 4 serologically distinct S. pyogenes strains were used: the serotype M1 S. pyogenes strain ATCC 700294 and the serotype M3 S. pyogenes strain ATCC12384 were obtained from the American Type Culture Collection (Manassas, VA, USA); the serotype M6 S. pyogenes SPY67 clinical isolate was provided by the Centre de recherche en infectiologie du Centre hospitalier de l'universit Laval, Sainte-Foy; and S. pyogenes strain B514 which was initially isolated from a mouse was provided by Susan Hollingshead, from University of Alabama, Birmingham. The E. coli strain XL1-Blue MRF' was used in these experiments as negative control. Chromosomal DNA was isolated from each S. pyogenes strain as previously described (Jayarao BM et al. 1991. J. Clin. Microbiol. 29:2774-2778). BVH-P2 (SEQ ID NO: 1) gene was amplified by PCR(ROBOCYCLER Gradient 96 Temperature cycler, Stratagene, La Jolla, CA) from the genomic DNA purified from the 4 S. pyogenes strains, and the control E. coli strain using the oligonucleotides primers DMAR124 and DMAR125 (Table 1). PCR was performed with 30 cycles of 45 sec at 95° C., 45 sec at 50° C. and 1 min at 72° C. and a final elongation period of 7 min at 72° C. The PCR products were size fractionated in 1% agarose gels and were visualized by ethidium bromide staining. The results of these PCR amplifications are presented in Table 2. The analysis of the amplification products revealed that BVH-P2 (SEQ ID NO: 1) gene was present in the genome of all of the 4 S. pyogenes strains tested. No such product was detected when the control E. coli DNA was submitted to identical PCR amplifications with these oligonucleotide primers.

TABLE 2

Identification of S. pyogenes genes by PCR amplification

| | Identification by PCR amplification of | | | | |
|---|---|---|---|---|---|
| Strain Identification | BVH-P2 | BVH-P3 | BVH-P4 | BVH-P5 | BVH-P6 |
| ATCC700294 (M1) | + | + | + | + | + |
| ATCC12384 (M3) | + | + | + | + | + |
| SPY67 (M6) | + | + | + | + | + |
| B514* | + | + | + | + | + |
| E. coli XL1 Blue MRF' | − | − | − | − | − |

*Mouse isolate

EXAMPLE 2

This Example Illustrates the Cloning and Molecular Characteristics of BVH-P3 Gene and Corresponding Polypeptide The coding region of S. pyogenes BVH-P3 gene (SEQ ID NO: 3) was amplified by PCR (ROBOCYCLER Gradient 96 Temperature cycler, Stratagene, La Jolla, CA) from genomic DNA of serotype M1 S. pyogenes strain ATCC700294 using the following oligos that contained base extensions for the addition of restriction sites NdeI (CATATG) and XhoI (CTCGAG): DMAR188 and DMAR189, which are presented in Table 1. The methods used for cloning BVH-P3 into an expression vector and sequencing are similar to the methods described in Example 1.

It was determined that the open reading frame (ORF) which codes for BVH-P3 contains 921-bp and encodes a 306 amino acid residues polypeptide with a predicted pI of 5.73 and a predicted molecular mass of 33,882.36 Da. Analysis of the predicted amino acid residues sequence (SEQ ID NO:4) using the Spscan software (Wisconsin Sequence Analysis Package; Genetics Computer Group) suggested the existence of a 27 amino acid residues signal peptide (MSLILGAFLS-VFLLVACSSTGTKTAKS)(SEQ ID NO: 44), which ends with a cleavage site situated between a serine and an aspartic acid residue. The BVH-P3 gene was shown to be present after PCR amplification using the oligonucleotide primers DMAR188 and DMAR189 in the 4 serologically S. pyogenes strains tested (Table 2). The methods used for PCR amplification of the BVH-P3 gene were similar to the methods presented in Example 1. No such product was detected when the control E. coli DNA was submitted to identical PCR amplifications with these oligonucleotide primers.

EXAMPLE 3

This Example Illustrates the Cloning and Molecular Characteristics of BVH-P4 Gene and Corresponding Polypeptide The coding region of S. pyogenes BVH-P4 gene (SEQ ID NO: 5) was amplified by PCR (ROBOCYCLER Gradient 96 Temperature cycler, STRATAGENE, La Jolla, CA) from genomic DNA of serotype M1 S. pyogenes strain ATCC700294 using the following oligos that contained base extensions for the addition of restriction sites NdeI (CATATG) and XhoI (CTCGAG): DMAR192 and DMAR193, which are presented in Table 1. The methods used for cloning BVH-P4 into an expression vector and sequencing are similar to the methods described in Example 1.

It was determined that the open reading frame (ORF) which codes for BVH-P4 contains 1053-bp and encodes a 350 amino acid residues polypeptide with a predicted pI of 7.90 and a predicted molecular mass of 36,392.50 Da. Analysis of the predicted amino acid residues sequence (SEQ ID NO:6) using the Spscan software (Wisconsin Sequence Analysis Package; Genetics Computer Group) suggested the existence of a 19 amino acid residues signal peptide (MNKKFIGLGLASVAVLSLA)(SEQ ID NO: 45), which ends with a cleavage site situated between two alanine residues.

The BVH-P4 gene was shown to be present after PCR amplification using the oligonucleotide primers DMAR192 and DMAR193 in the 4 serologically S. pyogenes strains tested (Table 2). The methods used for PCR amplification of the BVH-P4 gene were similar to the methods presented in Example 1. No such product was detected when the control E. coli DNA was submitted to identical PCR amplifications with these oligonucleotide primers.

Sequencing of additional BVH-P4 genes from other strains confirmed the high level of molecular conservation of this gene among S. pyogenes isolates. The respective coding region of S. pyogenes BVH-P4 gene from strains ATCC 12384 (SEQ ID NO: 11), SPY67 (SEQ ID NO: 13), and B514 (SEQ ID NO: 15) were amplified by PCR (ROBOCYCLER Gradient 96 Temperature cycler, STRATAGENE, La Jolla, CA) from genomic DNA using the oligonucleotide primers DMAR192 and DMAR193 which are described in Table 1. PCR products were purified from agarose gel using a QIAQUICK gel extraction kit from QIAGEN following the manufacturer's instructions (Chatsworth, CA) and the DNA inserts were sequenced (Taq Dye Deoxy Terminator Cycle Sequencing kit, ABI, Foster City, CA.). The predicted amino acid sequences from strains ATCC12384 (SEQ ID NO: 12), SPY67 (SEQ ID NO: 14), and p514 (SEQ ID NO: 16) were respectively presented in the following FIGS. 12, 14, and 16. The FIG. 18 depicts the consensus predicted amino acid sequences established for S. pyogenes BVH-P4. Pairwise comparison of these BVH-P4 amino acid sequences indicated that the level of identity was higher than 99% clearly showing the high level of conservation of BVH-P4 among S. pyogenes isolates.

EXAMPLE 4

This Example Illustrates the Cloning and Molecular Characteristics of BVH-P5 Gene and Corresponding Polypeptide The coding region of S. pyogenes BVH-P5 gene (SEQ ID NO: 7) was amplified by PCR (ROBOCYCLER Gradient 96 Temperature cycler, STRATAGENE, La Jolla, CA) from genomic DNA of serotype M1 S. pyogenes strain ATCC700294 using the following oligos that contained base extensions for the addition of restriction sites NdeI (CATATG) and XhoI (CTCGAG): DMAR200 and DMAR201, which are presented in Table 1. The methods used for cloning BVH-P5 into an expression vector and sequencing are similar to the methods described in Example 1.

It was determined that the open reading frame (ORF) which codes for BVH-P5 contains 1044-bp and encodes a 347 amino acid residues polypeptide with a predicted pI of 5.65 and a predicted molecular mass of 36,808.91 Da. Analysis of the predicted amino acid residues sequence (SEQ ID NO:8) using the Spscan software (Wisconsin Sequence Analysis Package; Genetics Computer Group) suggested the existence of a 17 amino acid residues signal peptide (MNKKVMSLGLVSTALFT)(SEQ ID NO: 46), which ends with a cleavage site situated between a threonine and a leucine residue.

The BVH-P5 gene was shown to be present after PCR amplification using the oligonucleotide primers DMAR200 and DMAR201 in the 4 serologically S. pyogenes strains tested,(Table 2). The methods used for PCR amplification of the BVH-P5 gene were similar to the methods presented in example 1. No such product was detected when the control E. coli DNA was submitted to identical PCR amplifications with these oligonucleotide primers.

EXAMPLE 5

This Example Illustrates the Cloning and Molecular Characteristics of BVH-P6 Gene and Corresponding Polypeptide The coding region of S. pyogenes BVH-P6 gene (SEQ ID NO:9) was amplified by PCR (ROBOCYCLER Gradient 96 Temperature cycler, STRATAGENE, La Jolla, CA) from genomic DNA of serotype M1 S. pyogenes strain ATCC700294 using the following oligonucleotide primers that contained base extensions for the addition of restriction sites NdeI (CATATG) and XhoI (CTCGAG): DMAR235 and DMAR236, which are presented in Table 1. The methods used for cloning BVH-P6 into an expression vector and sequencing are similar to the methods described in Example 1.

It was determined that the open reading frame (ORF) which codes for BVH-P6 contains 1020-bp and encodes a 339 amino acid residues polypeptide with a predicted pI of 6.66 and a predicted molecular mass of 38,017.78 Da. Analysis of the predicted amino acid residue sequence (SEQ ID NO:10) using the Spscan software (Wisconsin Sequence Analysis Package; Genetics Computer Group) suggested the existence of a 33 amino acid residue signal peptide (MRKRCYSTSAAVLAAVTLFVLSVDRGVIADSFS) (SEQ ID NO: 47), which ends with a cleavage site situated between a serine and an alanine residue. The BVH-P6 gene was shown to be present after PCR amplification using the oligonucleotide primers DMAR235 and DMAR236 in the 4 serologically S. pyogenes strains tested, (Table 2). The methods used for PCR amplification of the BVH-P6 gene were similar to the methods presented in example 1. No such product was detected when the control E. coli DNA was submitted to identical PCR amplifications with these oligonucleotide primers.

EXAMPLE 6

This Example Illustrates the Cloning of S. Pyogenes Genes in CMV Plasmid pCMV-GH The DNA coding regions of S. pyogenes proteins were inserted in phase downstream of a human growth hormone (hGH) gene which was under the transcriptional control of the cytomegalovirus (CMV) promotor in the plasmid vector PCMV-GH (Tang et al., Nature, 1992, 356 :152). The CMV promotor is a non functional plasmid in E. coli cells but active upon administration of the plasmid in eukaryotic cells. The vector also incorporated the ampicillin resistance gene.

The coding regions of BVH-P2 (SEQ ID NO: 1), BVH-P4 (SEQ ID NO: 5), BVH-P5 (SEQ ID NO: 7), and BVH-P6 (SEQ ID NO: 9) genes without their leader peptide regions were amplified by PCR (ROBOCYCLER Gradient 96 Temperature cycler, STRATAGENE, La Jolla, CA) from genomic DNA of serotype M1 S. pyogenes strain ATCC700294 using oligonucleotide primers that contained base extensions for the addition of restriction sites BamHI (GGATCC) and SalI (GTCGAC) which are described in Table 1. The PCR products were purified from agarose gel using a QIAQUICK gel extraction kit from QIAGEN (Chatsworth, CA), digested with restriction enzymes (PHARMACIA Canada Inc, Baie d'Urfe, Canada). The pCMV-GH vector (Laboratory of Dr. Stephen A. Johnston, Department of Biochemistry, The University of Texas, Dallas, Tex.) was digested with BamHI and SalI and purified from agarose gel using the QIAQUICK gel extraction kit from QIAGEN (Chatsworth, CA). The BamHI-SalI DNA fragments were ligated to the BamHI-SalI pCMV-GH vector to create the hGH-BVH-P2, hGH-BVHP-4, hGH-BVH-P5, and hGH-BVH-P6 fusion proteins under the control of the CMV promoter. The ligated products were transformed into E. coli strain DH5α [Φ8dlacZΔM15 Δ(lac-ZYA-argF)U169 endA1 recA1 hsdR17($r_K$–$m_K$+) deoR thi-1 supE44 λ⁻gyrA96 relA1] (Gibco BRL, Gaithersburg, Md.) according to the method of Simanis (Hanahan, D. DNA Cloning, 1985, D. M. Glover (ed), pp. 109-135). The recombinant pCMV plasmids were purified using a QIAGEN plasmid kit (Chatsworth, CA) and the nucleotide sequences of the DNA inserts were verified by DNA sequencing.

EXAMPLE 7

This Example Illustrates the use of DNA to Elicit an Immune Response to S. Pyogenes Protein Antigens Groups of 8 female BALB/c mice (Charles River, St-Constant, Québec, Canada) were immunized by intramuscular injection of 100 μl three times at two- or three-week intervals with 50 μg of recombinant pCMV-GH encoding BVH-P2 (SEQ ID NO: 1), BVH-P4 (SEQ ID NO: 5), BVH-P5 (SEQ ID NO: 7), and BVH-P6 (SEQ ID NO: 9) genes in presence of 50 μg of granulocyte-macrophage colony-stimulating factor (GM-CSF)-expressing plasmid pCMV-GH-GM-CSF (Laboratory of Dr. Stephen A. Johnston, Department of Biochemistry, The University of Texas, Dallas, Tex.). As control, groups of mice were injected with 50 μg of pCMV-GH in presence of 50 μg of pCMV-GH-GM-CSF. Blood samples were collected from the orbital sinus prior to each immunization and seven days following the third injection and serum antibody responses were determined by ELISA using the corresponding His-tagged labeled S. pyogenes recombinant proteins as coating antigens. The production and purification of these His-tagged labeled S. pyogenes recombinant proteins are presented in Example 8.

EXAMPLE 8

This Example Illustrates the Production and Purification of S. Pyogenes Recombinant Proteins The recombinant pET-21b(+)plasmids with BVH-P2 (SEQ ID NO: 1), BVH-P3 (SEQ ID NO: 3), BVH-P4 (SEQ ID NO: 5), BVH-P5 (SEQ ID NO: 7), and BVH-P6 (SEQ ID NO: 9) were used to transform by electroporation (GENE PULSER II apparatus, BIO-RAD Labs, Mississauga, Canada) E. coli strain BL21 (DE3) (F⁻ompT hsdS$_B$ ($r^-_B$m$^-_B$) gal dcm (DE3)) (NOVAGEN, Madison, WI). In this strain of E. coli, the T7 promoter controlling expression of the recombinant protein is specifically recognized by the T7 RNA polymerase (present on the λDE3 prophage) whose gene is under the control of the lac promoter which is inducible by isopropyl-β-d-thiogalactopyranoside (IPTG). The transformants BL21 (DE3)/rpET were grown at 37° C. with agitation at 250 rpm in LB broth (peptone 10 g/L, yeast extract 5 g/L, NaCl 10 g/L) containing 100 μg of carbenicillin (SIGMA-ALDRICH Canada Ltd., Oakville, Canada) per ml until the $A_{600}$ reached a value of 0.6. In order to induce the production of His-tagged S. pyogenes recombinant proteins, the cells were incubated for 3 additional hours in the presence of IPTG at a final concentration of 1 mM. Induced cells from a 500 ml culture were pelleted by centrifugation and frozen at −70° C.

The purification of the recombinant proteins from the soluble cytoplasmic fraction of IPTG-induced BL21(DE3)/rpET21b(+) was done by affinity chromatography based on the properties of the His•Tag sequence (6 consecutive histidine residues) to bind to divalent cations (Ni$^{2+}$) immobilized on the His•Bind metal chelation resin. Briefly, the pelleted cells obtained from a 500 mL culture induced with IPTG was resuspended in lysis buffer (20 mM Tris, 500 mM NaCl, 10 mM imidazole, pH 7.9) containing 1 mM PMSF, sonicated and centrifuged at 12,000×g for 20 min to remove debris. The supernatant was deposited on a Ni—NTA agarose column (QIAGEN, Mississauga, Ontario, Canada). The His•tag labeled S. pyogenes recombinant proteins were eluted with 250 mM imidazole-500 mM NaCl-20 mM Tris pH 7.9. The removal of the salt and imidazole from the samples was done by dialysis against PBS at 4° C. The quantities of recombinant proteins obtained from the soluble fraction of E. coli were estimated by MiCROBCA (quantitative assay)(Pierce, Rockford, Ill.).

EXAMPLE 9

This Example Illustrates the Reactivity of the His-Tagged S. Pyogenes Recombinant Proteins with Human Sera and Sera Collected from Mice after Immunization with S. Pyogenes Antigenic Preparations As shown in Table 3, all purified recombinant proteins were recognized in immunoblots by the antibodies present in the pool of normal sera. It indicates that humans which are normally in contact with S. pyogenes do develop antibodies that are specific to these proteins. These particular human antibodies might be implicated in the protection against S. pyogenes infection. In addition, immunoblots also revealed that sera collected from mice immunized with S. pyogenes antigenic preparation enriched membrane proteins which protected mice against lethal challenge also developed antibodies that recognized BVH-P3, BVH-P4 and BVH-P5 His-tagged recombinant proteins. This result indicates that these proteins were present in S. pyogenes antigenic preparation that protected mice against infection and that they induced antibodies that reacted with the corresponding His-tagged recombinant protein.

TABLE 3

Reactivity in immunoblots of human sera and sera collected from mice after immunization with S. pyogenes antigenic preparations with S. pyogenes His-tagged fusion recombinant proteins.

| Purified recombinant protein I.D.[1] | Apparent molecular weight (kDa)[2] | Reactivity in immunoblots with | |
|---|---|---|---|
| | | Human sera[3] | Mouse sera[4] |
| BVH-P2 | 25 | + | − |
| BVH-P3 | 34 | + | + |
| BVH-P4 | 35 | + | + |
| BVH-P5 | 34 | + | + |
| BVH-P6 | 35 | + | − |

[1]His-tagged recombinant proteins produced and purified as described in Example 7 were used to perform the immunoblots.
[2]Molecular weight of the His-tagged recombinant protein were estimated after SDS-PAGE.
[3]Two sera collected from healthy human volunteers were pooled together and diluted 1/500 to perform the immunoblots.
[4]Mouse sera collected after immunization with S. pyogenes antigenic preparations enriched membrane proteins were pooled and diluted 1/500 to perform the immunoblots. These mice were protected against a lethal S. pyogenes challenge.

EXAMPLE 10

This Example Illustrates the Accessibility to Antibodies of the S. Pyogenes BVH-P4 Polypeptide at the Surface of Intact Streptococcal Cells Bacteria were grown in Tood Hewitt (TH) broth (DIFCO Laboratories, Detroit, MI) with 0.5% Yeast extract (DIFCO Laboratories) and 0.5% peptone extract (MERCK, Darmstadt, Germany) at 37° C. in a 8% $CO_2$ atmosphere to give an $OD_{490\,nm}$ of 0.600 (~$10^8$ CFU/ml). Dilutions of anti-BVH-P4 or control sera were then added and allowed to bind to the cells, which were incubated for 2 h at 4° C. Samples were washed 4 times in blocking buffer [phosphate-buffered saline (PBS) containing 2% bovine serum albumin (BSA)], and then 1 ml of goat fluorescein (FITC)-conjugated anti-mouse IgG+IgM diluted in blocking buffer was added. After an additional incubation of 60 min at room temperature, samples were washed 4 times in blocking buffer and fixed with 0.25 % formaldehyde in PBS buffer for 18-24 h at 4° C. Cells were washed 2 times in PBS buffer and resuspended in 500 µl of PBS buffer. Cells were kept in the dark at 4° C. until analyzed by flow cytometry (EPICS® XL; BECKMAN COULTER, Inc.). Flow cytometric analysis revealed that BVH-P4-specific antibodies efficiently recognized their corresponding surface exposed epitopes on the heterologous (ATCC12384; serotype M3) S. pyogenes strain tested. It was determined that more than 90% of the 10,000 S. pyogenes cells analyzed were labeled with the antibodies present in the BVH-P4 specific anti-sera. It appears, that the BVH-P4 polypeptide is accessible at the surface where it can be recognized by antibodies.

EXAMPLE 11

This Example Illustrates the Protection Against Fatal S. Pyogenes Infection induced by Passive Immunization of Mice with Rabbit Hyper-Immune Sera New Zealand rabbits (Charles River laboratories, St-Constant, Canada) are injected subcutaneously at multiple sites with 50 µg and 100 µg of the different His•tagged S. pyogenes recombinant proteins that are produced and purified as described in Example 8 and adsorbed to ALHYDROGEL (aluminum hydroxide) adjuvant (Superfos® Biosector a/s). Rabbits are immunized three times at three-week intervals with the different His•tagged S. pyogenes recombinant proteins. Blood samples are collected three weeks after the third injection. The antibodies present in the serum are purified by precipitation using 40% saturated ammonium sulfate. Groups of 10 female CD-1 mice (Charles River) are injected intravenously with 500 µl of purified serum collected from rabbits immunized with the different His•tagged S. pyogenes recombinant proteins, or rabbits immunized with an unrelated control recombinant protein. Eighteen hours later the mice are challenged with approximately $2 \times 10^7$ CFU of the type 3 S. pyogenes strain ATCC12384. Samples of the S. pyogenes challenge inoculum are plated on blood agar plates to determine the CFU and to verify the challenge dose. Deaths are recorded for a period of 5 days.

EXAMPLE 12

This Example Illustrates the Protection of Mice Against Fatal S. Pyogenes Infection Induced by Immunization Groups of 8 female CD-1 mice (Charles River) are immunized subcutaneously three times at three-week intervals with 20 µg of affinity purified His-tagged S. pyogenes recombinant proteins in presence of 10 µg of QUILA (plant-derived saponin) adjuvant (Cedarlane Laboratories Ltd, Hornby, Canada) or, as control, with QUILA adjuvant alone in PBS. Blood samples are collected from the orbital sinus on day 1, 22 and 43 prior to each immunization and seven days (day 50) following the third injection. Two weeks later the mice are challenged with approximately $2 \times 10^7$ CFU of the type 3 S. pyogenes strain ATCC12384. Samples of the S. pyogenes challenge inoculum are plated on blood agar plates to determine the CFU and to verify the challenge dose. Deaths are recorded for a period of 14 days.

What is claimed is:

1. An isolated polypeptide comprising an amino acid sequence that is at least 90% identical to the full-length amino acid sequence set forth in SEQ ID NO: 10, wherein the isolated polypeptide is capable of inducing an immune response to *Streptococcus pyogenes*, and wherein the isolated polypeptide is capable of generating an antibody that specifically binds to a protein consisting of the amino acid sequence set forth in SEQ ID NO: 10.

2. The isolated polypeptide according to claim 1 wherein the polypeptide comprises an amino acid sequence at least 95% identical to the amino acid sequence set forth in SEQ ID NO: 10.

3. The isolated polypeptide according to claim 1 wherein the polypeptide comprises the amino acid sequence set forth in SEQ ID NO: 10.

4. The isolated polypeptide according to claim 3 from which the N-terminal methionine residue of SEQ ID NO: 10 is deleted.

5. An isolated polypeptide comprising an amino acid sequence that is at least 95% identical to the full-length amino acid sequence set forth in SLO ID NO: 10 from which the signal peptide amino acid sequence is deleted, wherein the signal peptide amino acid sequence is set forth in SEQ ID NO: 47.

6. A pharmaceutical composition comprising the isolated polypeptide according to any one of claims 1-5 and a pharmaceutically acceptable carrier or diluent.

7. The pharmaceutical composition according to claim 6 further comprising an adjuvant.

8. A kit comprising a polypeptide according to any one of claims 1-5 for detection or diagnosis of a *streptococcal* infection.

9. The kit according to claim 8 wherein the *streptococcal* infection is a *Streptococcus pyogenes* infection.

10. A method for therapeutic treatment of *Streptococcus pyogenes* bacterial infection in a host susceptible to *Streptococcus pyogenes* infection comprising administering to said host a therapeutic amount of a composition comprising the isolated polypeptide according to claim 1 and a pharmaceutically diluent or carrier.

11. The method according to claim 10 wherein the composition further comprises an adjuvant.

12. A method according to claim 10 wherein the host is a human or non-human animal.

* * * * *

UNITED STATES PATENT AND TRADEMARK OFFICE
CERTIFICATE OF CORRECTION

PATENT NO. : 7,595,057 B2  Page 1 of 1
APPLICATION NO. : 10/451337
DATED : September 29, 2009
INVENTOR(S) : Denis Martin It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1445 days.

Signed and Sealed this

Twenty-eighth Day of September, 2010

David J. Kappos
*Director of the United States Patent and Trademark Office*

SEQUENCE LISTING

<160> NUMBER OF SEQ ID NOS: 42

<210> SEQ ID NO 1
<211> LENGTH: 633
<212> TYPE: DNA
<213> ORGANISM: S. pyogenes

<400> SEQUENCE: 1

```
atgaaaaaga cattaacttt gctactggca ctctttgcca tcggggtaac tagtagcgtc    60
agagcggagg atgaacaaag tagtacacaa aagccagtaa aatttgattt ggatggacct   120
caacaaaaaa ttaaagatta tagtggcaac acaatcactc tagaagactt atatgttggt   180
agtaaagtag taaaaatata tatccctcaa ggatggtggg tatatcttta cagacaatgt   240
gatcataaca gtaaagaacg aggaattta gctagtccta ttctcgaaaa aaatataaca   300
aaaacagatc cttatcgtca atattataca ggagtacctt atattcttaa cttaggagaa   360
gatcctttga agaaggaga aaaattaact ttctcattta aaggagaaga cggatttat   420
gtcggtagct atatctatag agactctgat actataaaaa agaaaaaga agctgaagaa   480
gcacttcaaa aaaggaaga ggaaagcaa caaaacagc tagaagaaag catgctaaag   540
cagataagag aagaagacca taaaccttgg catcagcggt taagtgagag catccaagat   600
cagtggtgga actttaaggg actgtttcag tga                                 633
```

<210> SEQ ID NO 2
<211> LENGTH: 210
<212> TYPE: PRT
<213> ORGANISM: S. pyogenes

<400> SEQUENCE: 2

```
Met Lys Lys Thr Leu Thr Leu Leu Ala Leu Phe Ala Ile Gly Val
 1               5                  10                  15

Thr Ser Ser Val Arg Ala Glu Asp Glu Gln Ser Ser Thr Gln Lys Pro
                20                  25                  30

Val Lys Phe Asp Leu Asp Gly Pro Gln Gln Lys Ile Lys Asp Tyr Ser
            35                  40                  45

Gly Asn Thr Ile Thr Leu Glu Asp Leu Tyr Val Gly Ser Lys Val Val
        50                  55                  60

Lys Ile Tyr Ile Pro Gln Gly Trp Trp Val Tyr Leu Tyr Arg Gln Cys
65                  70                  75                  80

Asp His Asn Ser Lys Glu Arg Gly Ile Leu Ala Ser Pro Ile Leu Glu
                85                  90                  95

Lys Asn Ile Thr Lys Thr Asp Pro Tyr Arg Gln Tyr Tyr Thr Gly Val
            100                 105                 110

Pro Tyr Ile Leu Asn Leu Gly Glu Asp Pro Leu Lys Lys Gly Glu Lys
        115                 120                 125

Leu Thr Phe Ser Phe Lys Gly Glu Asp Gly Phe Tyr Val Gly Ser Tyr
    130                 135                 140

Ile Tyr Arg Asp Ser Asp Thr Ile Lys Lys Glu Lys Glu Ala Glu Glu
145                 150                 155                 160

Ala Leu Gln Lys Lys Glu Glu Lys Gln Gln Lys Gln Leu Glu Glu
                165                 170                 175

Ser Met Leu Lys Gln Ile Arg Glu Glu Asp His Lys Pro Trp His Gln
            180                 185                 190

Arg Leu Ser Glu Ser Ile Gln Asp Gln Trp Trp Asn Phe Lys Gly Leu
```

```
              195                 200                 205

Phe Gln
    210

<210> SEQ ID NO 3
<211> LENGTH: 921
<212> TYPE: DNA
<213> ORGANISM: S. pyogenes

<400> SEQUENCE: 3
atgagcctca tttttgggtgc ttttttatct gtttttctttt tagtagcttg ttcgtcaact      60
ggcactaaaa ctgctaagag tgataaatta aaagtcgtgg caaccaattc aattattgcc     120
gacatgacaa aagctattgc tggtgataaa atcgatctgc acagcattgt gccaatcggt     180
caagaccctc atgagtacga accattacca gaagatgttg aaaaaacaag taatgctgat     240
gtgattttct ataatggtat caatctagaa gatggcgggc aagcttggtt caccaaacta     300
gtgaaaaatg ctcaaaaaac gaaaaacaaa gattactttg ccgtgtctga tggcattgat     360
gtgatttact ggaaggtgc aagcgaaaaa ggaaaagaag atccacatgc ttggttaaat     420
ctcgaaaacg gaatcattta ttcaaaaaac attgccaaac aattgattgc aaaggatcct     480
aaaaacaaag aaacttatga aaagaaccta aaagcttatg tggctaaatt ggaaaaacta     540
gacaaagaag ccaaatcaaa atttgatgct attgcagaaa ataaaaaatt gattgtgact     600
agtgaaggct gcttcaagta ctttttcaaaa gcttacggtg tcccatctgc ttatatctgg     660
gaaattaaca ccgaagaaga aggaacacca gatcaaattt catcattgat tgaaaaacta     720
aaagtcatca agccatctgc gcttttttgta gagtcaagtg tcgatagacg ccctatggaa     780 actgttttcta aagatagtgg tattcctatt tattctgaga tctttacaga ttcaattgct     840
aaaaaaggta aacctggcga tagttattat gctatgatga aatggaacct tgacaaaatt     900
tctgaaggtc tagcaaaata a                                                921

<210> SEQ ID NO 4
<211> LENGTH: 306
<212> TYPE: PRT
<213> ORGANISM: S. pyogenes

<400> SEQUENCE: 4

Met Ser Leu Ile Leu Gly Ala Phe Leu Ser Val Phe Leu Leu Val Ala
  1               5                  10                  15

Cys Ser Ser Thr Gly Thr Lys Thr Ala Lys Ser Asp Lys Leu Lys Val
             20                  25                  30

Val Ala Thr Asn Ser Ile Ile Ala Asp Met Thr Lys Ala Ile Ala Gly
         35                  40                  45

Asp Lys Ile Asp Leu His Ser Ile Val Pro Ile Gly Gln Asp Pro His
     50                  55                  60

Glu Tyr Glu Pro Leu Pro Glu Asp Val Glu Lys Thr Ser Asn Ala Asp
 65                  70                  75                  80

Val Ile Phe Tyr Asn Gly Ile Asn Leu Glu Asp Gly Gly Gln Ala Trp
                 85                  90                  95

Phe Thr Lys Leu Val Lys Asn Ala Gln Lys Thr Lys Asn Lys Asp Tyr
            100                 105                 110

Phe Ala Val Ser Asp Gly Ile Asp Val Ile Tyr Leu Glu Gly Ala Ser
        115                 120                 125

Glu Lys Gly Lys Glu Asp Pro His Ala Trp Leu Asn Leu Glu Asn Gly
    130                 135                 140
```

```
Ile Ile Tyr Ser Lys Asn Ile Ala Lys Gln Leu Ile Ala Lys Asp Pro
145                 150                 155                 160

Lys Asn Lys Glu Thr Tyr Glu Lys Asn Leu Lys Ala Tyr Val Ala Lys
                165                 170                 175

Leu Glu Lys Leu Asp Lys Glu Ala Lys Ser Lys Phe Asp Ala Ile Ala
            180                 185                 190

Glu Asn Lys Lys Leu Ile Val Thr Ser Glu Gly Cys Phe Lys Tyr Phe
        195                 200                 205

Ser Lys Ala Tyr Gly Val Pro Ser Ala Tyr Ile Trp Glu Ile Asn Thr
210                 215                 220

Glu Glu Glu Gly Thr Pro Asp Gln Ile Ser Ser Leu Ile Glu Lys Leu
225                 230                 235                 240

Lys Val Ile Lys Pro Ser Ala Leu Phe Val Glu Ser Ser Val Asp Arg
                245                 250                 255

Arg Pro Met Glu Thr Val Ser Lys Asp Ser Gly Ile Pro Ile Tyr Ser
                260                 265                 270

Glu Ile Phe Thr Asp Ser Ile Ala Lys Lys Gly Lys Pro Gly Asp Ser
            275                 280                 285

Tyr Tyr Ala Met Met Lys Trp Asn Leu Asp Lys Ile Ser Glu Gly Leu
290                 295                 300

Ala Lys
305

<210> SEQ ID NO 5
<211> LENGTH: 1053
<212> TYPE: DNA
<213> ORGANISM: S. pyogenes

<400> SEQUENCE: 5
atgaacaaga aatttattgg tcttggttta gcgtcagtgg ctgtgctgag tttagctgct      60
tgtggtaatc gtggtgcttc taaaggtggg gcatcaggaa aaactgattt aaaagttgca     120
atggttaccg atactggtgg tgtagatgac aaatcattca accaatcagc atgggaaggc     180
ctgcaatctt ggggtaaaga atgggccttc aaaaaggaa caggtttcga ttattttcaa     240
tctacaagtg aatctgagta tgcaactaat ctcgatacag cagtttcagg agggtatcaa     300
ctgatttatg gtatcggctt tgcattgaaa gatgctattg ctaaagcagc tggagataat     360
gaaggagtta gtttgttat tatcgatgat attatcgaag aaaagataa tgtagccagt      420 gttacctttg ccgaccatga agctgcttat cttgcaggaa ttgcagctgc aaaaacaaca     480
aaaacaaaaa cagttggttt cgtgggcggt atggaaggaa ctgtcataac tcgatttgaa     540
aaaggttttg aagcaggagt taagtctgtt gacgatacaa tccaagttaa agttgattat     600
gctggatcat ttggtgacgc tgcaaaagga aaaacaatcg cagcagctca gtatgcagca     660
ggtgctgatg ttatttacca ggcagcagga ggcactggag caggtgtatt taatgaagca     720
aaagctatta tgaaaaacg tagtgaagct gataagtttt gggttattgg tgttgaccgt     780
gatcaaaaag acgaaggaaa atacacttct aaagatggca agaagcaaa ctttgtactt     840 gcatcatcaa tcaaagaagt cggtaaagct gttcagttaa tcaacaagca agtagcagat     900
aaaaaattcc ctgaggaaa aacaactgtc tatggtctaa agatggcgg tgttgaaatc     960 gcaactacaa atgtttcaaa agaagctgtt aaagctatta agaagcgaa agcaaaaatt    1020 aaatctggtg acattaaagt tcctgaaaaa tag                                1053
```

<210> SEQ ID NO 6
<211> LENGTH: 344
<212> TYPE: PRT
<213> ORGANISM: S. pyogenes

<400> SEQUENCE: 6

```
Asn Lys Lys Phe Ile Gly Leu Gly Leu Ala Ser Val Ala Val Leu Ser
 1               5                  10                  15

Leu Ala Ala Cys Gly Asn Arg Gly Ala Ser Lys Gly Gly Ala Ser Gly
             20                  25                  30

Lys Thr Asp Leu Lys Val Ala Met Val Thr Asp Thr Gly Gly Val Asp
         35                  40                  45

Asp Lys Ser Phe Asn Gln Ser Ala Trp Glu Gly Gln Ser Trp Gly Lys
     50                  55                  60

Glu Met Gly Leu Gln Lys Gly Thr Gly Phe Asp Tyr Phe Gln Ser Thr
 65                  70                  75                  80

Ser Glu Ser Glu Tyr Ala Thr Asn Leu Asp Thr Ala Val Ser Gly Gly
                 85                  90                  95

Tyr Gln Leu Ile Tyr Gly Ile Gly Phe Ala Leu Lys Asp Ala Ile Ala
            100                 105                 110

Lys Ala Ala Gly Asp Asn Gly Val Lys Phe Val Ile Asp Asp Ile
        115                 120                 125

Ile Glu Gly Lys Asp Asn Val Ala Ser Val Thr Phe Ala Asp His Glu
    130                 135                 140

Ala Ala Tyr Leu Ala Gly Ile Ala Ala Ala Lys Thr Thr Lys Thr Lys
145                 150                 155                 160

Thr Val Gly Phe Val Gly Gly Met Glu Gly Thr Val Ile Thr Arg Phe
                165                 170                 175

Glu Gly Phe Glu Ala Gly Val Lys Ser Val Asp Asp Thr Ile Gln Val
            180                 185                 190

Lys Val Asp Tyr Ala Gly Ser Phe Gly Asp Ala Ala Lys Gly Lys Thr
        195                 200                 205

Ile Ala Ala Ala Gln Tyr Ala Ala Gly Ala Asp Val Ile Tyr Gln Ala
    210                 215                 220

Ala Gly Gly Thr Gly Ala Gly Val Phe Asn Glu Ala Ala Ile Asn Glu
225                 230                 235                 240

Lys Arg Ser Glu Ala Asp Lys Val Trp Val Ile Gly Val Asp Arg Asp
                245                 250                 255

Gln Lys Asp Glu Gly Lys Tyr Thr Ser Lys Asp Gly Lys Glu Ala Asn
            260                 265                 270

Phe Val Leu Ala Ser Ser Ile Lys Glu Val Gly Lys Ala Val Gln Leu
        275                 280                 285

Ile Asn Lys Gln Val Ala Asp Lys Phe Pro Gly Gly Lys Thr Thr Val
    290                 295                 300

Tyr Gly Leu Lys Asp Gly Gly Val Glu Ile Ala Thr Thr Asn Val Ser
305                 310                 315                 320

Lys Glu Ala Val Lys Ala Ile Lys Glu Ala Lys Ala Lys Ile Lys Ser
                325                 330                 335

Gly Asp Ile Lys Val Pro Glu Lys
            340
```

<210> SEQ ID NO 7
<211> LENGTH: 1044
<212> TYPE: DNA
<213> ORGANISM: S. pyogenes -continued

```
<400> SEQUENCE: 7
atgaacaaaa aagtaatgtc acttggtctt gtttcgactg ccctattcac attaggaggc      60
tgtaccaata actccgctaa acaaacaact gacaattcat taaaaatcgc tatgattact     120
aatcagacgg gtattgatga caagtcattt aaccagtcag cctgggaagg cttacaagct     180
tggggaaaag aaaataaact tgaaaaagga aaaggctatg attatttcca atcagccaat     240
gaatcagagt ttaccacaaa ccttgagtca gcagtaacca atggttataa tcttgttttt     300
gggattggat ttccattaca tgacgctgta gaaaaagtag ccgcaaacaa tcctgacaac     360 catttttgcaa ttgtggatga tgtgattaaa ggtcaaaaaa atgttgcaag tatcaccttt     420
tcagaccatg aagcggcata cctagccggt gttgcagcag ctaaaacgac aaaaaccaag     480
caagttggtt ttgtaggtgg tatggaagga gatgttgtca gcgctttga aaaaggtttt      540 gaagctggtg tgaaatcagt agatgatacc atcaaagtaa gagttgctta tgcaggctct     600
tttgcagatg ctgccaaagg caagacgatt gcagctgctc aatacgctga aggcgcagat     660
gttatttatc atgcagcagg aggcacaggg gcgggtgtct ttagcgaagc taagtctatc     720
aacgaaaaac gtaagaaga agataaggtt tgggttattg gtgttgaccg tgaccaaagt     780
gaagatggaa aatacactac aaaagatggc aagtcagcta attttgtttt gacctcaagt     840
atcaaggaag tcggaaaagc tttagtaaaa gtagccgtaa aaacctcaga agaccaattc     900
ccaggtggtc aaataaccac ttttggttta aagaaggtg gtgttagcct tacaacggat     960
gctctgacac aagacactaa aaaagctatt gaggctgcta aaaagcgat tatcgaagga    1020 accatcacag ttcctgaaaa ctaa                                         1044

<210> SEQ ID NO 8
<211> LENGTH: 347
<212> TYPE: PRT
<213> ORGANISM: S. pyogenes

<400> SEQUENCE: 8

Met Asn Lys Lys Val Met Ser Leu Gly Leu Val Ser Thr Ala Leu Phe
  1               5                  10                  15

Thr Leu Gly Gly Cys Thr Asn Asn Ser Ala Lys Gln Thr Thr Asp Asn
             20                  25                  30

Ser Leu Lys Ile Ala Met Ile Thr Asn Gln Thr Gly Ile Asp Asp Lys
         35                  40                  45

Ser Phe Asn Gln Ser Ala Trp Glu Gly Leu Gln Ala Trp Gly Lys Glu
     50                  55                  60

Asn Lys Leu Glu Lys Gly Lys Gly Tyr Asp Tyr Phe Gln Ser Ala Asn
 65                  70                  75                  80

Glu Ser Glu Phe Thr Thr Asn Leu Glu Ser Ala Val Thr Asn Gly Tyr
                 85                  90                  95

Asn Leu Val Phe Gly Ile Gly Phe Pro Leu His Asp Ala Val Glu Lys
            100                 105                 110

Val Ala Ala Asn Asn Pro Asp Asn His Phe Ala Ile Val Asp Asp Val
        115                 120                 125

Ile Lys Gly Gln Lys Asn Val Ala Ser Ile Thr Phe Ser Asp His Glu
    130                 135                 140

Ala Ala Tyr Leu Ala Gly Val Ala Ala Ala Lys Thr Thr Lys Thr Lys
145                 150                 155                 160

Gln Val Gly Phe Val Gly Gly Met Glu Gly Asp Val Val Lys Arg Phe
                165                 170                 175
```

Glu Lys Gly Phe Glu Ala Gly Val Lys Ser Val Asp Asp Thr Ile Lys
            180                 185                 190

Val Arg Val Ala Tyr Ala Gly Ser Phe Ala Asp Ala Ala Lys Gly Lys
        195                 200                 205

Thr Ile Ala Ala Ala Gln Tyr Ala Glu Gly Ala Asp Val Ile Tyr His
    210                 215                 220

Ala Ala Gly Gly Thr Gly Ala Gly Val Phe Ser Glu Ala Lys Ser Ile
225                 230                 235                 240

Asn Glu Lys Arg Lys Glu Glu Asp Lys Val Trp Val Ile Gly Val Asp
            245                 250                 255

Arg Asp Gln Ser Glu Asp Gly Lys Tyr Thr Thr Lys Asp Gly Lys Ser
        260                 265                 270

Ala Asn Phe Val Leu Thr Ser Ser Ile Lys Glu Val Gly Lys Ala Leu
    275                 280                 285

Val Lys Val Ala Val Lys Thr Ser Glu Asp Gln Phe Pro Gly Gly Gln
290                 295                 300

Ile Thr Thr Phe Gly Leu Lys Glu Gly Val Ser Leu Thr Thr Asp
305                 310                 315                 320

Ala Leu Thr Gln Asp Thr Lys Lys Ala Ile Glu Ala Ala Lys Lys Ala
            325                 330                 335

Ile Ile Glu Gly Thr Ile Thr Val Pro Glu Asn
            340                 345

<210> SEQ ID NO 9
<211> LENGTH: 1020
<212> TYPE: DNA
<213> ORGANISM: S. pyogenes

<400> SEQUENCE: 9
atgagaaaaa gatgctattc aacttcagct gcagtattgg cagcagtgac tttatttgtt      60
ctatcggtag atcgtggtgt tatagcagat agttttctg ctaatcaaga gattagatat      120
tcggaagtaa caccttatca cgttacttcc gtttggacca aggagttac tcctccagca      180
aacttcactc aaggtgaaga tgtttttcac gctcccttatg ttgctaacca aggatggtat      240
gatattacca aaacattcaa tggaaaagac gatcttcttt gcggggctgc cacagcaggg      300
aatatgcttc actggtggtt cgatcaaaac aaagaccaaa ttaaacgtta tttggaagag      360
catccagaaa agcaaaaaat aaacttcaat ggcgaacaga tgtttgacgt aaaagaagct      420
atcgacacta aaaccacca gctagatagt aaattatttg aatattttaa agaaaaagct      480
ttcccttatc tatctactaa acacctagga gttttccctg atcatgtaat tgatatgttc      540
attaacggct accgcttag tctaactaac cacggtccaa cgccagtaaa agaaggtagt      600
aaagatcccc gaggtggtat ttttgacgcc gtatttacaa gaggtgatca agtaagcta      660
ttgacaagtc gtcatgattt taagaaaaa aatctcaaag aaatcagtga tctcattaag      720
aaagagttaa ccgaaggcaa ggctctaggc ctatcacaca cctacgctaa cgtacgcatc      780
aaccatgtta taaacctgtg gggagctgac tttgattcta cgggaacct taaagctatt      840
tatgtaacag actctgatag taatgcatct attggtatga agaaatactt tgttggtgtt      900
aattccgctg gaaagtagc tatttctgct aaagaaataa aagaagataa tattggtgct      960
caagtactag ggttatttac actttcaaca gggcaagata gttggaatca gaccaattaa     1020

<210> SEQ ID NO 10
<211> LENGTH: 339
<212> TYPE: PRT

<213> ORGANISM: S. pyogenes

<400> SEQUENCE: 10

```
Met Arg Lys Arg Cys Tyr Ser Thr Ser Ala Ala Val Leu Ala Ala Val
1               5                   10                  15

Thr Leu Phe Val Leu Ser Val Asp Arg Gly Val Ile Ala Asp Ser Phe
            20                  25                  30

Ser Ala Asn Gln Glu Ile Arg Tyr Ser Glu Val Thr Pro Tyr His Val
        35                  40                  45

Thr Ser Val Trp Thr Lys Gly Val Thr Pro Ala Asn Phe Thr Gln
    50                  55                  60

Gly Glu Asp Val Phe His Ala Pro Tyr Val Ala Asn Gln Gly Trp Tyr
65                  70                  75                  80

Asp Ile Thr Lys Thr Phe Asn Gly Lys Asp Asp Leu Leu Cys Gly Ala
                85                  90                  95

Ala Thr Ala Gly Asn Met Leu His Trp Trp Phe Asp Gln Asn Lys Asp
            100                 105                 110

Gln Ile Lys Arg Tyr Leu Glu Glu His Pro Glu Lys Gln Lys Ile Asn
        115                 120                 125

Phe Asn Gly Glu Gln Met Phe Asp Val Lys Glu Ala Ile Asp Thr Lys
    130                 135                 140

Asn His Gln Leu Asp Ser Lys Leu Phe Glu Tyr Phe Lys Glu Lys Ala
145                 150                 155                 160

Phe Pro Tyr Leu Ser Thr Lys His Leu Gly Val Phe Pro Asp His Val
                165                 170                 175

Ile Asp Met Phe Ile Asn Gly Tyr Arg Leu Ser Leu Thr Asn His Gly
            180                 185                 190

Pro Thr Pro Val Lys Glu Gly Ser Lys Asp Pro Arg Gly Gly Ile Phe
        195                 200                 205

Asp Ala Val Phe Thr Arg Gly Asp Gln Ser Lys Leu Leu Thr Ser Arg
    210                 215                 220

His Asp Phe Lys Glu Lys Asn Leu Lys Glu Ile Ser Asp Leu Ile Lys
225                 230                 235                 240

Lys Glu Leu Thr Glu Gly Lys Ala Leu Gly Leu Ser His Thr Tyr Ala
                245                 250                 255

Asn Val Arg Ile Asn His Val Ile Asn Leu Trp Gly Ala Asp Phe Asp
            260                 265                 270

Ser Asn Gly Asn Leu Lys Ala Ile Tyr Val Thr Asp Ser Asp Ser Asn
        275                 280                 285

Ala Ser Ile Gly Met Lys Lys Tyr Phe Val Gly Val Asn Ser Ala Gly
    290                 295                 300

Lys Val Ala Ile Ser Ala Lys Glu Ile Lys Glu Asp Asn Ile Gly Ala
305                 310                 315                 320

Gln Val Leu Gly Leu Phe Thr Leu Ser Thr Gly Gln Asp Ser Trp Asn
                325                 330                 335

Gln Thr Asn
```

<210> SEQ ID NO 11
<211> LENGTH: 976
<212> TYPE: DNA
<213> ORGANISM: S. pyogenes

<400> SEQUENCE: 11
cttggtttag cgtcagtggc tgtgctgagt ttagctgctt gtggtaatcg tggtgcttca    60

-continued

```
aaggtggggc atcaggaaaa actgatttaa aagttgcaat ggttaccgat actggtgggt    120
agatgacaaa tcattcaacc aatcagcatg ggaaggcctg caatcttggg gtaaagaatg    180
ggccttcaaa aaggaacagg tttcgattat tttcaatcta caagtgaatc tgagtagcaa    240
ctaatcttga tacagcagtt tcaggagggt atcaactgat ttatggtatc ggcttgcatt    300
gaaagatgct attgctaaag cagctggaga taatgaagga gttaagtttg ttatatcgat    360
gatattatcg aaggaaaaga taatgtagcc agtgttacct ttgctgacca tgagctgctt    420
atcttgcagg aattgcagct gcaaaaacaa caaaaacaaa aacagttggt ttgtgggcgg    480 tatgaagga actgtcataa ctcgatttga aaaaggtttt gaagcaggag taagtctgtt    540
gacgatacaa tccaagttaa agttgattat gctggatcat ttggtgacgc gcaaaaggaa    600
aaacaatcgc agcagctcag tatgcagcag gtgctgatgt tatttaccag cagcaggagg    660
cactggagca ggtgtattta atgaagcaaa agctattaat gaaaacgag tgaagctgat    720 aaagtttggg ttattggtgt tgaccgtgat caaaaagacg aaggaaatac acttctaaag    780
atggcaaaga agcaaacttt gtacttgcat catcaatcaa agaagtggta agctgttca    840 gttaatcaac aaacaagtag cagataaaaa attccctgga ggaaaacaac tgtctatggt    900
ctaaaagatg gcggtgttga aatcgcaact acaaatgttt caagaagct gttaaagcta    960 ttaaagaagc gaaagc                                                    976
```

<210> SEQ ID NO 12
<211> LENGTH: 330
<212> TYPE: PRT
<213> ORGANISM: S. pyogenes

<400> SEQUENCE: 12

```
Leu Gly Leu Ala Ser Val Ala Val Leu Ser Leu Ala Ala Cys Gly Asn
  1               5                  10                  15

Arg Gly Ala Ser Lys Gly Ala Ser Gly Lys Thr Asp Leu Lys Val
             20                  25                  30

Ala Met Val Thr Asp Thr Gly Gly Val Asp Asp Lys Ser Phe Asn Gln
         35                  40                  45

Ser Ala Trp Glu Gly Leu Gln Ser Trp Gly Lys Glu Met Gly Leu Gln
     50                  55                  60

Lys Gly Thr Gly Phe Asp Tyr Phe Gln Ser Thr Glu Ser Glu Tyr
 65                  70                  75                  80

Ala Thr Asn Leu Asp Thr Ala Val Ser Gly Gly Tyr Gln Leu Ile Tyr
                 85                  90                  95

Gly Ile Gly Phe Ala Leu Lys Asp Ala Ile Ala Lys Ala Gly Asp
            100                 105                 110

Asn Glu Gly Val Lys Phe Val Ile Asp Ile Glu Gly Lys
        115                 120                 125

Asp Asn Val Ala Ser Val Thr Phe Ala Asp His Glu Ala Ala Tyr Leu
    130                 135                 140

Ala Gly Ile Ala Ala Lys Thr Thr Lys Thr Lys Thr Val Gly Phe
145                 150                 155                 160

Val Gly Gly Met Glu Gly Thr Val Ile Thr Arg Phe Glu Lys Gly Phe
                165                 170                 175

Glu Ala Gly Val Lys Ser Val Asp Asp Thr Ile Gln Val Lys Val Asp
            180                 185                 190

Tyr Ala Gly Ser Phe Gly Asp Ala Ala Lys Gly Lys Thr Ile Ala Ala
        195                 200                 205
```

```
Ala Gln Tyr Ala Ala Gly Ala Asp Val Ile Tyr Gln Ala Ala Gly Gly
    210                 215                 220

Thr Gly Ala Gly Val Phe Asn Glu Ala Lys Ala Ile Asn Glu Lys Arg
225                 230                 235                 240

Ser Glu Ala Asp Lys Val Trp Val Ile Gly Val Asp Arg Asp Gln Lys
                245                 250                 255

Asp Glu Gly Lys Tyr Thr Ser Lys Asp Gly Lys Glu Ala Asn Phe Val
                260                 265                 270

Leu Ala Ser Ser Ile Lys Glu Val Gly Lys Ala Val Gln Leu Ile Asn
                275                 280                 285

Lys Gln Val Ala Asp Lys Lys Phe Pro Gly Gly Lys Thr Thr Val Tyr
    290                 295                 300

Gly Leu Lys Asp Gly Gly Val Glu Ile Ala Thr Thr Asn Val Ser Lys
305                 310                 315                 320

Glu Ala Val Lys Ala Ile Lys Glu Ala Lys
                325                 330

<210> SEQ ID NO 13
<211> LENGTH: 993
<212> TYPE: DNA
<213> ORGANISM: S. pyogenes

<400> SEQUENCE: 13
tcttggttta gcgtcagtgg ctgtgctgag tttagctgct tgtggtaatc gtggtgcttc      60
taaaggtggg gcatcaggaa aaactgattt aaaagttgca atggttaccg atactggtgg     120
tgtagatgac aaatcattca accaatcagc atgggaaggc ctgcaatctt ggggtaaaga     180
aatgggcctt caaaaggaa caggtttcga ttattttcaa tctacaagtg aatctgagta     240
tgcaactaat ctcgatacag cagtttcagg aggatatcaa ctgatttatg gtatcggctt     300
tgcattgaaa gatgctattg ctaaagcagc tggagataat gaaggagtta agtttgttat     360
tatcgatgat attatcgaag gaaaagataa tgtagccagt gttacctttg ccgaccatga     420
agctgcttat cttgcaggaa ttgcggctgc aaaaacaaca aaaacaaaaa cagttggttt     480
cgtgggcggt atggaaggaa ctgtcataac tcgatttgaa aaaggttttg aagcaggagt     540
taagtctgtt gacgatacaa tccaagttaa agttgattat gctggatcat tggtgacgc      600 tgcaaaagga aaaacaatcg cagcagctca gtatgcagca ggtgctgatg ttatttacca     660
ggcagcagga ggcactggag caggtgtatt taatgaagca aaagctatta atgaaaaacg     720
tagtgaagct gataaagttt gggttattgg tgttgaccgt gatcaaaaag acgaaggaaa     780
atacacttct aaagatggca agaagcaaa ctttgtactt gcatcatcaa tcaaagaagt     840
tggtaaagct gttcagttaa tcaacaaaca agtagcagat aaaaaattcc ctggaggaaa     900
aacaactgtc tatggtttaa agatggcgg tgttgaaatc gcaactacaa atgtttcaaa     960
agaagctgtt aaagctatta agaagcgaa agc                                  993

<210> SEQ ID NO 14
<211> LENGTH: 330
<212> TYPE: PRT
<213> ORGANISM: S. pyogenes

<400> SEQUENCE: 14

Leu Gly Leu Ala Ser Val Ala Val Leu Ser Leu Ala Ala Cys Gly Asn
 1               5                  10                  15

Arg Gly Ala Ser Lys Gly Gly Ala Ser Gly Lys Thr Asp Leu Lys Val
            20                  25                  30
```

```
Ala Met Val Thr Asp Thr Gly Gly Val Asp Asp Lys Ser Phe Asn Gln
             35                  40                  45
Ser Ala Trp Glu Gly Leu Gln Ser Trp Gly Lys Glu Met Gly Leu Gln
 50                  55                  60
Lys Gly Thr Gly Phe Asp Tyr Phe Gln Ser Thr Ser Glu Ser Glu Tyr
 65                  70                  75                  80
Ala Thr Asn Leu Asp Thr Ala Val Ser Gly Tyr Gln Leu Ile Tyr
                 85                  90                  95
Gly Ile Gly Phe Ala Leu Lys Asp Ala Ile Ala Lys Ala Ala Gly Asp
                100                 105                 110
Asn Glu Gly Val Lys Phe Val Ile Ile Asp Ile Ile Glu Gly Lys
            115                 120                 125
Asp Asn Val Ala Ser Val Thr Phe Ala Asp His Glu Ala Ala Tyr Leu
130                 135                 140
Ala Gly Ile Ala Ala Ala Lys Thr Thr Lys Thr Lys Thr Val Gly Phe
145                 150                 155                 160
Val Gly Gly Met Glu Gly Thr Val Ile Thr Arg Phe Glu Lys Gly Phe
                165                 170                 175
Glu Ala Gly Val Lys Ser Val Asp Asp Thr Ile Gln Val Lys Val Asp
                180                 185                 190
Tyr Ala Gly Ser Phe Gly Asp Ala Ala Lys Gly Lys Thr Ile Ala Ala
                195                 200                 205
Ala Gln Tyr Ala Ala Gly Ala Asp Val Ile Tyr Gln Ala Ala Gly Gly
            210                 215                 220
Thr Gly Ala Gly Val Phe Asn Glu Ala Lys Ala Ile Asn Glu Lys Arg
225                 230                 235                 240
Ser Glu Ala Asp Lys Val Trp Val Ile Gly Val Asp Arg Asp Gln Lys
                245                 250                 255
Asp Glu Gly Lys Tyr Thr Ser Lys Asp Gly Lys Glu Ala Asn Phe Val
                260                 265                 270
Leu Ala Ser Ser Ile Lys Glu Val Gly Lys Ala Val Gln Leu Ile Asn
            275                 280                 285
Lys Gln Val Ala Asp Lys Lys Phe Pro Gly Gly Lys Thr Thr Val Tyr
290                 295                 300
Gly Leu Lys Asp Gly Gly Val Glu Ile Ala Thr Thr Asn Val Ser Lys
305                 310                 315                 320
Glu Ala Val Lys Ala Ile Lys Glu Ala Lys
                325                 330

<210> SEQ ID NO 15
<211> LENGTH: 993
<212> TYPE: DNA
<213> ORGANISM: S. pyogenes

<400> SEQUENCE: 15
tcttggttta gcgtcagtgg ctgtgctgag tttagctgct tgtggtaatc gtggtgcttc      60
taaaggtggg gcagcaggaa aaactgattt aaaagttgca atggttaccg atactggtgg     120
tgtagatgat aaatcattca accaatcagc atgggaaggc ctgcaatctt ggggtaaaga     180
aatgggcctt caaaaggaa caggtttcga ttattttcaa tctacaagtg aatctgagta     240
tgcaactaat ctcgatacag cagtttcagg agggtatcaa ctgatttatg gtatcggctt     300
tgcattgaaa gatgctattg ctaaagcagc tggagataat gaaggagtta agtttgttat     360
tatcgatgat attatcgaag gaaaagataa tgtagccagt gttacctttg ccgaccatga     420
```

-continued

```
agctgcttat cttgcaggaa ttgcagctgc aaaaacaaca aaaacaaaaa cagttggttt      480
cgtgggcggt atggaaggaa ctgtcataac tcgatttgaa aaaggttttg aagcaggagt      540
taagtctgtt gacgatacaa tccaagttaa agttgattat gctggatcat tggtgacgc      600 tgcaaaagga aaacaatcg cagcagctca gtatgcagca ggtgctgatg ttatttacca      660
ggcagcagga ggcactggag caggtgtatt taatgaagca aaagctatta atgaaaaacg      720
tagtgaagct gataaagttt gggttattgg tgttgaccgt gatcaaaaag acgaaggaaa      780
atacacttct aaagatggca agaagcaaa ctttgtactt gcatcatcaa tcaaagaagt      840
tggtaaagct gttcagttaa tcaacaagca agtagcagat aaaaaattcc ctggaggaaa      900
aacaactgtc tatggtctaa aagatggcgg tgttgaaatc gcaactacaa atgtttcaaa      960
agaagctgtt aaagctatta agaagcgaa agc                                   993
```

<210> SEQ ID NO 16
<211> LENGTH: 330
<212> TYPE: PRT
<213> ORGANISM: S. pyogenes

<400> SEQUENCE: 16

```
Leu Gly Leu Ala Ser Val Ala Val Leu Ser Leu Ala Ala Cys Gly Asn
  1               5                  10                  15

Arg Gly Ala Ser Lys Gly Gly Ala Ala Gly Lys Thr Asp Leu Lys Val
             20                  25                  30

Ala Met Val Thr Asp Thr Gly Gly Val Asp Asp Lys Ser Phe Asn Gln
         35                  40                  45

Ser Ala Trp Glu Gly Leu Gln Ser Trp Gly Lys Glu Met Gly Leu Gln
     50                  55                  60

Lys Gly Thr Gly Phe Asp Tyr Phe Gln Ser Thr Ser Glu Ser Glu Tyr
 65                  70                  75                  80

Ala Thr Asn Leu Asp Thr Ala Val Ser Gly Gly Tyr Gln Leu Ile Tyr
                 85                  90                  95

Gly Ile Gly Phe Ala Leu Lys Asp Ala Ile Ala Lys Ala Ala Gly Asp
            100                 105                 110

Asn Glu Gly Val Lys Phe Val Ile Asp Asp Ile Glu Gly Lys
        115                 120                 125

Asp Asn Val Ala Ser Val Thr Phe Ala Asp His Glu Ala Ala Tyr Leu
    130                 135                 140

Ala Gly Ile Ala Ala Ala Lys Thr Thr Lys Thr Lys Thr Val Gly Phe
145                 150                 155                 160

Val Gly Gly Met Glu Gly Thr Val Ile Thr Arg Phe Glu Lys Gly Phe
                165                 170                 175

Glu Ala Gly Val Lys Ser Val Asp Asp Thr Ile Gln Val Lys Val Asp
            180                 185                 190

Tyr Ala Gly Ser Phe Gly Asp Ala Lys Gly Lys Thr Ile Ala Ala
        195                 200                 205

Ala Gln Tyr Ala Ala Gly Ala Asp Val Ile Tyr Gln Ala Ala Gly Gly
    210                 215                 220

Thr Gly Ala Gly Val Phe Asn Glu Ala Lys Ala Ile Asn Glu Lys Arg
225                 230                 235                 240

Ser Glu Ala Asp Lys Val Trp Val Ile Gly Val Asp Arg Asp Gln Lys
                245                 250                 255

Asp Glu Gly Lys Tyr Thr Ser Lys Asp Gly Lys Glu Ala Asn Phe Val
            260                 265                 270
```

```
Leu Ala Ser Ser Ile Lys Glu Val Gly Lys Ala Val Gln Leu Ile Asn
        275                 280                 285

Lys Gln Val Ala Asp Lys Lys Phe Pro Gly Gly Lys Thr Thr Val Tyr
        290                 295                 300

Gly Leu Lys Asp Gly Gly Val Glu Ile Ala Thr Thr Asn Val Ser Lys
305                 310                 315                 320

Glu Ala Val Lys Ala Ile Lys Glu Ala Lys
                325                 330

<210> SEQ ID NO 17
<211> LENGTH: 29
<212> TYPE: DNA
<213> ORGANISM: Artificial Sequence
<220> FEATURE:
<223> OTHER INFORMATION: primer DMAR124

<400> SEQUENCE: 17
cggagagaac atatgaaaaa gacattaac                                    29

<210> SEQ ID NO 18
<211> LENGTH: 28
<212> TYPE: DNA
<213> ORGANISM: Artificial Sequence
<220> FEATURE:
<223> OTHER INFORMATION: primer DMAR125

<400> SEQUENCE: 18
gggctcgagc tgaaacagtc ccttaaag                                     28

<210> SEQ ID NO 19
<211> LENGTH: 22
<212> TYPE: DNA
<213> ORGANISM: Artificial Sequence
<220> FEATURE:
<223> OTHER INFORMATION: primer DMAR507

<400> SEQUENCE: 19
gagcggatcc tgaacaaagt ag                                           22

<210> SEQ ID NO 20
<211> LENGTH: 28
<212> TYPE: DNA
<213> ORGANISM: Artificial Sequence
<220> FEATURE:
<223> OTHER INFORMATION: primer DMAR508

<400> SEQUENCE: 20
ggggtcgacc tgaaacagtc ccttaaag                                     28

<210> SEQ ID NO 21
<211> LENGTH: 28
<212> TYPE: DNA
<213> ORGANISM: Artificial Sequence
<220> FEATURE:
<223> OTHER INFORMATION: primer DMAR188

<400> SEQUENCE: 21
gatgggaaag catatgagcc tcattttg                                     28

<210> SEQ ID NO 22
<211> LENGTH: 25
<212> TYPE: DNA
<213> ORGANISM: Artificial Sequence
<220> FEATURE:
```

```
<223> OTHER INFORMATION: primer DMAR189

<400> SEQUENCE: 22
ggctcgagtt ttgctagacc ttcag                                    25

<210> SEQ ID NO 23
<211> LENGTH: 32
<212> TYPE: DNA
<213> ORGANISM: Artificial Sequence
<220> FEATURE:
<223> OTHER INFORMATION: primer DMAR192

<400> SEQUENCE: 23
gggttcatac atatgaacaa gaaatttatt gg                            32

<210> SEQ ID NO 24
<211> LENGTH: 27
<212> TYPE: DNA
<213> ORGANISM: Artificial Sequence
<220> FEATURE:
<223> OTHER INFORMATION: primer DMAR193

<400> SEQUENCE: 24
ggctcgagtt tttcaggaac tttaatg                                  27

<210> SEQ ID NO 25
<211> LENGTH: 25
<212> TYPE: DNA
<213> ORGANISM: Artificial Sequence
<220> FEATURE:
<223> OTHER INFORMATION: primer DMAR509

<400> SEQUENCE: 25
gtttggatcc ttgtggtaat cgtgg                                    25

<210> SEQ ID NO 26
<211> LENGTH: 27
<212> TYPE: DNA
<213> ORGANISM: Artificial Sequence
<220> FEATURE:
<223> OTHER INFORMATION: primer DMAR510

<400> SEQUENCE: 26
gggtcgactt tttcaggaac tttaatg                                  27

<210> SEQ ID NO 27
<211> LENGTH: 31
<212> TYPE: DNA
<213> ORGANISM: Artificial Sequence
<220> FEATURE:
<223> OTHER INFORMATION: primer DMAR200

<400> SEQUENCE: 27
ggttcatttt catatgaaca aaaaagtaat g                             31

<210> SEQ ID NO 28
<211> LENGTH: 28
<212> TYPE: DNA
<213> ORGANISM: Artificial Sequence
<220> FEATURE:
<223> OTHER INFORMATION: primer DMAR201

<400> SEQUENCE: 28
ggctcgaggt tttcaggaac tgtgatgg                                 28
```

<210> SEQ ID NO 29
<211> LENGTH: 29
<212> TYPE: DNA
<213> ORGANISM: Artificial Sequence
<220> FEATURE:
<223> OTHER INFORMATION: primer DMAR511

<400> SEQUENCE: 29
ggggatccta ccaataactc cgctaaaca                                    29

<210> SEQ ID NO 30
<211> LENGTH: 31
<212> TYPE: DNA
<213> ORGANISM: Artificial Sequence
<220> FEATURE:
<223> OTHER INFORMATION: primer DMAR512

<400> SEQUENCE: 30
caggtcgact tttcaggaac tgtgatggtt c                                 31

<210> SEQ ID NO 31
<211> LENGTH: 30
<212> TYPE: DNA
<213> ORGANISM: Artificial Sequence
<220> FEATURE:
<223> OTHER INFORMATION: primer DMAR235

<400> SEQUENCE: 31
ggatagtttt catatgaatc aagagattag                                   30

<210> SEQ ID NO 32
<211> LENGTH: 29
<212> TYPE: DNA
<213> ORGANISM: Artificial Sequence
<220> FEATURE:
<223> OTHER INFORMATION: primer DMAR236

<400> SEQUENCE: 32
ccctcgagat tggtctgatt ccaactatc                                    29

<210> SEQ ID NO 33
<211> LENGTH: 30
<212> TYPE: DNA
<213> ORGANISM: Artificial Sequence
<220> FEATURE:
<223> OTHER INFORMATION: primer DMAR513

<400> SEQUENCE: 33
tttggatcct aatcaagaga ttagatattc                                   30

<210> SEQ ID NO 34
<211> LENGTH: 29
<212> TYPE: DNA
<213> ORGANISM: Artificial Sequence
<220> FEATURE:
<223> OTHER INFORMATION: primer DMAR514

<400> SEQUENCE: 34
ccgtcgacat tggtctgatt ccaactatc                                    29

<210> SEQ ID NO 35
<211> LENGTH: 993
<212> TYPE: DNA
<213> ORGANISM: S. pyogenes

<400> SEQUENCE: 35

-continued

| | |
|---|---|
| tcttggttta gcgtcagtgg ctgtgctgag tttagctgct tgtggtaatc gtggtgcttc | 60 |
| taaaggtggg gcatcaggaa aaactgattt aaaagttgca atggttaccg atactggtgg | 120 |
| tgtagatgac aaatcattca accaatcagc atgggaaggc ctgcaatctt ggggtaaaga | 180 |
| aatgggcctt caaaaaggaa caggtttcga ttatttttcaa tctacaagtg aatctgagta | 240 |
| tgcaactaat ctcgatacag cagtttcagg agggtatcaa ctgatttatg gtatcggctt | 300 |
| tgcattgaaa gatgctattg ctaaagcagc tggagataat gaaggagtta agtttgttat | 360 |
| tatcgatgat attatcgaag gaaaagataa tgtagccagt gttacctttg ccgaccatga | 420 |
| agctgcttat cttgcaggaa ttgcagctgc aaaaacaaca aaaacaaaaa cagttggttt | 480 |
| cgtgggcggt atggaaggaa ctgtcataac tcgatttgaa aaaggttttg aagcaggagt | 540 |
| taagtctgtt gacgatacaa tccaagttaa agttgattat gctggatcat tggtgacgc | 600 |
| tgcaaaagga aaaacaatcg cagcagctca gtatgcagca ggtgctgatg ttatttacca | 660 |
| ggcagcagga ggcactggag caggtgtatt taatgaagca aaagctatta atgaaaaacg | 720 |
| tagtgaagct gataaagttt gggttattgg tgttgaccgt gatcaaaaag acgaaggaaa | 780 |
| atacacttct aaagatggca agaagcaaa ctttgtactt gcatcatcaa tcaaagaagt | 840 |
| cggtaaagct gttcagttaa tcaacaagca agtagcagat aaaaaattcc ctggaggaaa | 900 |
| aacaactgtc tatggtctaa aagatggcgg tgttgaaatc gcaactacaa atgtttcaaa | 960 |
| agaagctgtt aaagctatta agaagcgaa agc | 993 |

<210> SEQ ID NO 36
<211> LENGTH: 993
<212> TYPE: DNA
<213> ORGANISM: S. pyogenes

<400> SEQUENCE: 36

| | |
|---|---|
| tcttggttta gcgtcagtgg ctgtgctgag tttagctgct tgtggtaatc gtggtgcttc | 60 |
| taaaggtggg gcatcaggaa aaactgattt aaaagttgca atggttaccg atactggtgg | 120 |
| tgtagatgac aaatcattca accaatcagc atgggaaggc ctgcaatctt ggggtaaaga | 180 |
| aatgggcctt caaaaaggaa caggtttcga ttatttttcaa tctacaagtg aatctgagta | 240 |
| tgcaactaat cttgatacag cagtttcagg agggtatcaa ctgatttatg gtatcggctt | 300 |
| tgcattgaaa gatgctattg ctaaagcagc tggagataat gaaggagtta agtttgttat | 360 |
| tatcgatgat attatcgaag gaaaagataa tgtagccagt gttacctttg ctgaccatga | 420 |
| agctgcttat cttgcaggaa ttgcagctgc aaaaacaaca aaaacaaaaa cagttggttt | 480 |
| cgtgggcggt atggaaggaa ctgtcataac tcgatttgaa aaaggttttg aagcaggagt | 540 |
| taagtctgtt gacgatacaa tccaagttaa agttgattat gctggatcat tggtgacgc | 600 |
| tgcaaaagga aaaacaatcg cagcagctca gtatgcagca ggtgctgatg ttatttacca | 660 |
| ggcagcagga ggcactggag caggtgtatt taatgaagca aaagctatta atgaaaaacg | 720 |
| tagtgaagct gataaagttt gggttattgg tgttgaccgt gatcaaaaag acgaaggaaa | 780 |
| atacacttct aaagatggca agaagcaaa ctttgtactt gcatcatcaa tcaaagaagt | 840 |
| tggtaaagct gttcagttaa tcaacaaaca agtagcagat aaaaaattcc ctggaggaaa | 900 |
| aacaactgtc tatggtctaa aagatggcgg tgttgaaatc gcaactacaa atgtttcaaa | 960 |
| agaagctgtt aaagctatta agaagcgaa agc | 993 |

<210> SEQ ID NO 37
<211> LENGTH: 993

<210> SEQ ID NO 37
<211> LENGTH: 993
<212> TYPE: DNA
<213> ORGANISM: S. pyogenes

<400> SEQUENCE: 37

```
tcttggttta gcgtcagtgg ctgtgctgag tttagctgct tgtggtaatc gtggtgcttc    60
taaaggtggg gcatcaggaa aaactgattt aaaagttgca atggttaccg atactggtgg   120
tgtagatgac aaatcattca accaatcagc atgggaaggc ctgcaatctt ggggtaaaga   180
aatgggcctt caaaaaggaa caggtttcga ttattttcaa tctacaagtg aatctgagta   240
tgcaactaat ctcgatacag cagtttcagg aggatatcaa ctgatttatg gtatcggctt   300
tgcattgaaa gatgctattg ctaaagcagc tggagataat gaaggagtta agtttgttat   360
tatcgatgat attatcgaag gaaaagataa tgtagccagt gttacctttg ccgaccatga   420
agctgcttat cttgcaggaa ttgcggctgc aaaaacaaca aaaacaaaaa cagttggttt   480
cgtgggcggt atggaaggaa ctgtcataac tcgatttgaa aaaggttttg aagcaggagt   540
taagtctgtt gacgatacaa tccaagttaa agttgattat gctggatcat tggtgacgc    600
tgcaaaagga aaacaatcg cagcagctca gtatgcagca ggtgctgatg ttatttacca   660
ggcagcagga ggcactggag caggtgtatt taatgaagca aaagctatta tgaaaaacg    720
tagtgaagct gataaagttt gggttattgg tgttgaccgt gatcaaaaag acgaaggaaa   780
atacacttct aaagatggca agaagcaaa ctttgtactt gcatcatcaa tcaaagaagt   840
tggtaaagct gttcagttaa tcaacaaaca agtagcagat aaaaaattcc ctggaggaaa   900
aacaactgtc tatggtttaa aagatggcgg tgttgaaatc gcaactacaa atgtttcaaa   960
agaagctgtt aaagctatta agaagcgaa agc                                 993
```

<210> SEQ ID NO 38
<211> LENGTH: 993
<212> TYPE: DNA
<213> ORGANISM: Mouse

<400> SEQUENCE: 38

```
tcttggttta gcgtcagtgg ctgtgctgag tttagctgct tgtggtaatc gtggtgcttc    60
taaaggtggg gcagcaggaa aaactgattt aaaagttgca atggttaccg atactggtgg   120
tgtagatgat aaatcattca accaatcagc atgggaaggc ctgcaatctt ggggtaaaga   180
aatgggcctt caaaaaggaa caggtttcga ttattttcaa tctacaagtg aatctgagta   240
tgcaactaat ctcgatacag cagtttcagg agggtatcaa ctgatttatg gtatcggctt   300
tgcattgaaa gatgctattg ctaaagcagc tggagataat gaaggagtta agtttgttat   360
tatcgatgat attatcgaag gaaaagataa tgtagccagt gttacctttg ccgaccatga   420
agctgcttat cttgcaggaa ttgcagctgc aaaaacaaca aaaacaaaaa cagttggttt   480
cgtgggcggt atggaaggaa ctgtcataac tcgatttgaa aaaggttttg aagcaggagt   540
taagtctgtt gacgatacaa tccaagttaa agttgattat gctggatcat tggtgacgc    600
tgcaaaagga aaacaatcg cagcagctca gtatgcagca ggtgctgatg ttatttacca   660
ggcagcagga ggcactggag caggtgtatt taatgaagca aaagctatta tgaaaaacg    720
tagtgaagct gataaagttt gggttattgg tgttgaccgt gatcaaaaag acgaaggaaa   780
atacacttct aaagatggca agaagcaaa ctttgtactt gcatcatcaa tcaaagaagt   840
tggtaaagct gttcagttaa tcaacaagca agtagcagat aaaaaattcc ctggaggaaa   900
aacaactgtc tatggtctaa aagatggcgg tgttgaaatc gcaactacaa atgtttcaaa   960
```
agaagctgtt aaagctatta agaagcgaa agc    993

<210> SEQ ID NO 39
<211> LENGTH: 330
<212> TYPE: PRT
<213> ORGANISM: S. pyogenes

<400> SEQUENCE: 39

Leu Gly Leu Ala Ser Val Ala Val Leu Ser Leu Ala Ala Cys Gly Asn
1               5                   10                  15

Arg Gly Ala Ser Lys Gly Gly Ala Ser Gly Lys Thr Asp Leu Lys Val
            20                  25                  30

Ala Met Val Thr Asp Thr Gly Gly Val Asp Asp Lys Ser Phe Asn Gln
        35                  40                  45

Ser Ala Trp Glu Gly Leu Gln Ser Trp Gly Lys Glu Met Gly Leu Gln
    50                  55                  60

Lys Gly Thr Gly Phe Asp Tyr Phe Gln Ser Thr Ser Glu Ser Glu Tyr
65                  70                  75                  80

Ala Thr Asn Leu Asp Thr Ala Val Ser Gly Gly Tyr Gln Leu Ile Tyr
                85                  90                  95

Gly Ile Gly Phe Ala Leu Lys Asp Ala Ile Ala Lys Ala Ala Gly Asp
            100                 105                 110

Asn Glu Gly Val Lys Phe Val Ile Ile Asp Asp Ile Ile Glu Gly Lys
        115                 120                 125

Asp Asn Val Ala Ser Val Thr Phe Ala Asp His Glu Ala Ala Tyr Leu
    130                 135                 140

Ala Gly Ile Ala Ala Lys Thr Thr Lys Thr Lys Thr Val Gly Phe
145                 150                 155                 160

Val Gly Gly Met Glu Gly Thr Val Ile Thr Arg Phe Glu Lys Gly Phe
                165                 170                 175

Glu Ala Gly Val Lys Ser Val Asp Asp Thr Ile Gln Val Lys Val Asp
            180                 185                 190

Tyr Ala Gly Ser Phe Gly Asp Ala Ala Lys Gly Lys Thr Ile Ala Ala
        195                 200                 205

Ala Gln Tyr Ala Ala Gly Ala Asp Val Ile Tyr Gln Ala Ala Gly Gly
    210                 215                 220

Thr Gly Ala Gly Val Phe Asn Glu Ala Lys Ala Ile Asn Glu Lys Arg
225                 230                 235                 240

Ser Glu Ala Asp Lys Val Trp Val Ile Gly Val Asp Arg Asp Gln Lys
                245                 250                 255

Asp Glu Gly Lys Tyr Thr Ser Lys Asp Gly Lys Glu Ala Asn Phe Val
            260                 265                 270

Leu Ala Ser Ser Ile Lys Glu Val Gly Lys Ala Val Gln Leu Ile Asn
        275                 280                 285

Lys Gln Val Ala Asp Lys Lys Phe Pro Gly Gly Lys Thr Thr Val Tyr
    290                 295                 300

Gly Leu Lys Asp Gly Gly Val Glu Ile Ala Thr Thr Asn Val Ser Lys
305                 310                 315                 320

Glu Ala Val Lys Ala Ile Lys Glu Ala Lys
                325                 330

<210> SEQ ID NO 40
<211> LENGTH: 330
<212> TYPE: PRT
<213> ORGANISM: S. pyogenes

<400> SEQUENCE: 40

```
Leu Gly Leu Ala Ser Val Ala Val Leu Ser Leu Ala Ala Cys Gly Asn
  1               5                  10                  15

Arg Gly Ala Ser Lys Gly Gly Ala Ser Gly Lys Thr Asp Leu Lys Val
             20                  25                  30

Ala Met Val Thr Asp Thr Gly Val Asp Asp Lys Ser Phe Asn Gln
         35                  40                  45

Ser Ala Trp Glu Gly Leu Gln Ser Trp Gly Lys Glu Met Gly Leu Gln
 50                  55                  60

Lys Gly Thr Gly Phe Asp Tyr Phe Gln Ser Thr Ser Glu Ser Glu Tyr
 65                  70                  75                  80

Ala Thr Asn Leu Asp Thr Ala Val Ser Gly Gly Tyr Gln Leu Ile Tyr
                 85                  90                  95

Gly Ile Gly Phe Ala Leu Lys Asp Ala Ile Ala Lys Ala Ala Gly Asp
                100                 105                 110

Asn Glu Gly Val Lys Phe Val Ile Ile Asp Asp Ile Ile Glu Gly Lys
                115                 120                 125

Asp Asn Val Ala Ser Val Thr Phe Ala Asp His Glu Ala Ala Tyr Leu
130                 135                 140

Ala Gly Ile Ala Ala Ala Lys Thr Thr Lys Thr Lys Thr Val Gly Phe
145                 150                 155                 160

Val Gly Gly Met Glu Gly Thr Val Ile Thr Arg Phe Glu Lys Gly Phe
                165                 170                 175

Glu Ala Gly Val Lys Ser Val Asp Asp Thr Ile Gln Val Lys Val Asp
                180                 185                 190

Tyr Ala Gly Ser Phe Gly Asp Ala Ala Lys Gly Lys Thr Ile Ala Ala
                195                 200                 205

Ala Gln Tyr Ala Ala Gly Ala Asp Val Ile Tyr Gln Ala Ala Gly Gly
            210                 215                 220

Thr Gly Ala Gly Val Phe Asn Glu Ala Lys Ala Ile Asn Glu Lys Arg
225                 230                 235                 240

Ser Glu Ala Asp Lys Val Trp Val Ile Gly Val Asp Arg Asp Gln Lys
                245                 250                 255

Asp Glu Gly Lys Tyr Thr Ser Lys Asp Gly Lys Glu Ala Asn Phe Val
                260                 265                 270

Leu Ala Ser Ser Ile Lys Glu Val Gly Lys Ala Val Gln Leu Ile Asn
                275                 280                 285

Lys Gln Val Ala Asp Lys Phe Pro Gly Gly Lys Thr Thr Val Tyr
            290                 295                 300

Gly Leu Lys Asp Gly Gly Val Glu Ile Ala Thr Thr Asn Val Ser Lys
305                 310                 315                 320

Glu Ala Val Lys Ala Ile Lys Glu Ala Lys
                325                 330
```

<210> SEQ ID NO 41
<211> LENGTH: 330
<212> TYPE: PRT
<213> ORGANISM: S. pyogenes

<400> SEQUENCE: 41

```
Leu Gly Leu Ala Ser Val Ala Val Leu Ser Leu Ala Ala Cys Gly Asn
  1               5                  10                  15

Arg Gly Ala Ser Lys Gly Gly Ala Ser Gly Lys Thr Asp Leu Lys Val
             20                  25                  30
```

```
Ala Met Val Thr Asp Thr Gly Gly Val Asp Asp Lys Ser Phe Asn Gln
            35                  40                  45

Ser Ala Trp Glu Gly Leu Gln Ser Trp Gly Lys Glu Met Gly Leu Gln
 50                  55                  60

Lys Gly Thr Gly Phe Asp Tyr Phe Gln Ser Thr Ser Glu Ser Glu Tyr
 65                  70                  75                  80

Ala Thr Asn Leu Asp Thr Ala Val Ser Gly Gly Tyr Gln Leu Ile Tyr
                 85                  90                  95

Gly Ile Gly Phe Ala Leu Lys Asp Ala Ile Ala Lys Ala Ala Gly Asp
            100                 105                 110

Asn Glu Gly Val Lys Phe Val Ile Asp Asp Ile Glu Gly Lys
            115                 120                 125

Asp Asn Val Ala Ser Val Thr Phe Ala Asp His Glu Ala Ala Tyr Leu
130                 135                 140

Ala Gly Ile Ala Ala Lys Thr Thr Lys Thr Lys Thr Val Gly Phe
145                 150                 155                 160

Val Gly Gly Met Glu Gly Thr Val Ile Thr Arg Phe Glu Lys Gly Phe
            165                 170                 175

Glu Ala Gly Val Lys Ser Val Asp Asp Thr Ile Gln Val Lys Val Asp
            180                 185                 190

Tyr Ala Gly Ser Phe Gly Asp Ala Ala Lys Gly Lys Thr Ile Ala Ala
            195                 200                 205

Ala Gln Tyr Ala Ala Gly Ala Asp Val Ile Tyr Gln Ala Ala Gly Gly
            210                 215                 220

Thr Gly Ala Gly Val Phe Asn Glu Ala Lys Ala Ile Asn Glu Lys Arg
225                 230                 235                 240

Ser Glu Ala Asp Lys Val Trp Val Ile Gly Val Asp Arg Asp Gln Lys
                245                 250                 255

Asp Glu Gly Lys Tyr Thr Ser Lys Asp Gly Lys Glu Ala Asn Phe Val
            260                 265                 270

Leu Ala Ser Ser Ile Lys Glu Val Gly Lys Ala Val Gln Leu Ile Asn
            275                 280                 285

Lys Gln Val Ala Asp Lys Lys Phe Pro Gly Gly Lys Thr Thr Val Tyr
290                 295                 300

Gly Leu Lys Asp Gly Gly Val Glu Ile Ala Thr Thr Asn Val Ser Lys
305                 310                 315                 320

Glu Ala Val Lys Ala Ile Lys Glu Ala Lys
                325                 330

<210> SEQ ID NO 42
<211> LENGTH: 330
<212> TYPE: PRT
<213> ORGANISM: Mouse

<400> SEQUENCE: 42

Leu Gly Leu Ala Ser Val Ala Val Leu Ser Leu Ala Ala Cys Gly Asn
 1               5                  10                  15

Arg Gly Ala Ser Lys Gly Gly Ala Ala Gly Lys Thr Asp Leu Lys Val
            20                  25                  30

Ala Met Val Thr Asp Thr Gly Gly Val Asp Asp Lys Ser Phe Asn Gln
            35                  40                  45

Ser Ala Trp Glu Gly Leu Gln Ser Trp Gly Lys Glu Met Gly Leu Gln
 50                  55                  60

Lys Gly Thr Gly Phe Asp Tyr Phe Gln Ser Thr Ser Glu Ser Glu Tyr
 65                  70                  75                  80
```

-continued

```
Ala Thr Asn Leu Asp Thr Ala Val Ser Gly Gly Tyr Gln Leu Ile Tyr
            85                  90                  95

Gly Ile Gly Phe Ala Leu Lys Asp Ala Ile Ala Lys Ala Ala Gly Asp
            100                 105                 110

Asn Glu Gly Val Lys Phe Val Ile Ile Asp Asp Ile Ile Glu Gly Lys
            115                 120                 125

Asp Asn Val Ala Ser Val Thr Phe Ala Asp His Glu Ala Ala Tyr Leu
            130                 135                 140

Ala Gly Ile Ala Ala Lys Thr Thr Lys Thr Lys Thr Val Gly Phe
145                 150                 155                 160

Val Gly Gly Met Glu Gly Thr Val Ile Thr Arg Phe Glu Lys Gly Phe
                165                 170                 175

Glu Ala Gly Val Lys Ser Val Asp Asp Thr Ile Gln Val Lys Val Asp
            180                 185                 190

Tyr Ala Gly Ser Phe Gly Asp Ala Ala Lys Gly Lys Thr Ile Ala Ala
            195                 200                 205

Ala Gln Tyr Ala Ala Gly Ala Asp Val Ile Tyr Gln Ala Ala Gly Gly
        210                 215                 220

Thr Gly Ala Gly Val Phe Asn Glu Ala Lys Ala Ile Asn Glu Lys Arg
225                 230                 235                 240

Ser Glu Ala Asp Lys Val Trp Val Ile Gly Val Asp Arg Asp Gln Lys
            245                 250                 255

Asp Glu Gly Lys Tyr Thr Ser Lys Asp Gly Lys Glu Ala Asn Phe Val
            260                 265                 270

Leu Ala Ser Ser Ile Lys Glu Val Gly Lys Ala Val Gln Leu Ile Asn
        275                 280                 285

Lys Gln Val Ala Asp Lys Lys Phe Pro Gly Gly Lys Thr Thr Val Tyr
        290                 295                 300

Gly Leu Lys Asp Gly Gly Val Glu Ile Ala Thr Thr Asn Val Ser Lys
305                 310                 315                 320

Glu Ala Val Lys Ala Ile Lys Glu Ala Lys
            325                 330
```